US006593093B1

(12) United States Patent
Uhl et al.

(10) Patent No.: US 6,593,093 B1
(45) Date of Patent: Jul. 15, 2003

(54) DETECTION OF GROUP A STREPTOCOCCUS

(75) Inventors: James R. Uhl, Rochester, MN (US); Franklin R. Cockerill, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 10/081,923

(22) Filed: Feb. 20, 2002

(51) Int. Cl.[7] .................................................. C12Q 1/68
(52) U.S. Cl. .......................................................... 435/6
(58) Field of Search ........................... 435/6, 803, 91.2; 436/501, 800, 56; 935/77, 78; 537/27; 514/4; 536/23.1, 24.3

(56) References Cited

U.S. PATENT DOCUMENTS

| | | | | |
|---|---|---|---|---|
| 4,683,195 A | | 7/1987 | Mullis et al. | |
| 4,683,202 A | | 7/1987 | Mullis | |
| 4,800,159 A | | 1/1989 | Mullis et al. | |
| 4,965,188 A | | 10/1990 | Mullis et al. | |
| 4,996,143 A | | 2/1991 | Heller et al. | |
| 5,035,996 A | | 7/1991 | Hartley | |
| 5,565,322 A | * | 10/1996 | Heller | 435/6 |
| 5,683,896 A | | 11/1997 | Hartley et al. | |
| 5,849,489 A | | 12/1998 | Heller | |
| 5,945,313 A | | 8/1999 | Hartley et al. | |
| 6,001,564 A | * | 12/1999 | Bergeron et al. | 435/6 |
| 6,162,603 A | | 12/2000 | Heller | |
| 6,287,781 B1 | * | 9/2001 | Lee et al. | 435/6 |

FOREIGN PATENT DOCUMENTS

| | | |
|---|---|---|
| WO | WO 97/46707 | 12/1997 |
| WO | WO 97/46712 | 12/1997 |
| WO | WO 97/46714 | 12/1997 |

OTHER PUBLICATIONS

GenBank Accession No. AE004092.

GenBank Accession No. NC_002737 (copy on CD–Rom).

Alam et al., "PCR–Based Methods for Genotyping Viridans Group Streptococci," *J. Clin. Microbiol.,* 1999, 37(9):2772–2776.

Anhalt et al., "Comparison of Three Methods for Detection of Group A Streptococci in Throat Swabs," *J. Clin. Microbiol.,* 1992, 30(8):2135–2138.

Artiushin and Timoney, "PCR for Detection of *Streptococcus equi,*" *Adv. Exp. Med. Biol.,* 1997, 418:359–361.

Bentley and Leigh, "Development of PCR–Based Hybridization Protocol for Identification of Streptococcal Species," *J. Clin. Microbiol.,* 1995, 33(5):1296–1301.

Bessen et al., "Molecular Markers for Throat and Skin Isolates of Group A Streptococci," *Adv. Exp. Med. Biol.,* 1997, 418:537–543.

Ferritti et al., "Complete genome sequence of an MI strain of *Streptococcus pyogens,*" *Proc. Natl. Acad. Sci. USA,* 2001, 98(8):4658–4663.

Garnier et al., "Identification of Clinically Relevant Viridans Group Streptococci to the Species Level by PCR," *J. Clin. Microbiol.,* 1997, 35(9):2337–2341.

Luesink et al., "Molecular Characterization of the *Lactococcus lactis* ptsHI Operon and Analysis of the Regulatory Role of HPr," *J. Bacteriology,* 1999, 18(3)P764–771.

McClelland et al., "Length Polymorphisms in tRNA Intergenic Spacers Detected by Using the Polymerase Chain Reaction Can Distiguish Streptococcal Strains and Species," *J. Clin. Microbiol.,* 1992, 30(6):1499–1504.

Steed et al., "Rapid Detection of *Streptococuss pyrgenes* in Pediatric Patient Specimens by DNA Probe," *J. Clin. Microbiol.,* 1993, 31(11):2996–3000.

Vadeboncoeur et al., "Regulation of the pts Operon in Low G+C Gram–Positive Bacteria," *J. Mol. Microbiol. Biotechnol.,* 2000, 2(4):483–490.

Ferretti et al., Complete genome sequence of an M1 strain of *Steptococcus pyogenes,* PNAS, Apr. 10, 2001, vol. 98, No. 8, 4658–4663.*

* cited by examiner

*Primary Examiner*—Ethan Whisenant
*Assistant Examiner*—Shar Hashemi
(74) *Attorney, Agent, or Firm*—Fish & Richardson P.C., P.A.

(57) ABSTRACT

The invention provides methods to detect Group A Streptococcus (GAS) in biological samples using real-time PCR. Primers and probes for the detection of GAS are provided by the invention. Articles of manufacture containing such primers and probes for detecting GAS are further provided by the invention.

35 Claims, 11 Drawing Sheets

Figure 1A

```
pts BHGAS OU         #1     --- --- --- --- --- --- --- --- --- --- --- ---
                     #1     ATG ACA GAA ATG CTT AAA GGA ATT GCA GCC TCA GAC
                            MET Thr Glu MET Leu Lys Gly Ile Ala Ala Ser Asp

pts BHGAS OU         #37    --- --- --- --- --- --- --- --- --- --- --- ---
                     #37    GGC GTT GCT GTT GCT AAA GCA TAT CTA CTA GTT CAG
                            Gly Val Ala Val Ala Lys Ala Tyr Leu Leu Val Gln

pts BHGAS OU         #73    --- --- --- --- --- --- --- --- --- --- --- ---
                     #73    CCG GAT TTG TCA TTT GAG ACT GTT ACA GTC GCA GAT
                            Pro Asp Leu Ser Phe Glu Thr Val Thr Val Ala Asp

pts BHGAS OU         #109   --- --- --- --- --- --- --- --- --- --- --- ---
                     #109   ACA AAT GCA GAA GAA GCT CGC CTT GAT GTT GCA CTC
                            Thr Asn Ala Glu Glu Ala Arg Leu Asp Val Ala Leu

pts BHGAS OU         #145   --- --- --- --- --- --- --- --- --- --- --- ---
pts group A #6       >#1>                                   --- --- --- ---
pts Group A #5       >#1>                                 - --- --- --- ---
pts Group A #7       >#1>                                 - --- --- --- ---
pts group A #8       >#1>                                   --- --- --- ---
pts Group A #9       >#1>               --- --- --- --- --- --- --- --- ---
pts group A #4       >#1>                                   --- --- --- ---
pts Group A #10      >#1>                                   --- --- --- ---
pts Group A #3       >#1>                                 - --- --- --- ---
pts group A #1       >#1>                                 - --- --- --- ---
pts Group A #11      >#1>                                 - --- --- --- ---
                     #145   CAA GCT GCA CAA GAC GAG CTT TCT GTT ATC CGT GAA
                            Gln Ala Ala Gln Asp Glu Leu Ser Val Ile Arg Glu

pts BHGAS OU         #181   --- --- --- --- --- --- --- --- --- --- --- ---
pts group A #6       #13    --- --- --- --- --- --- --- --- --- --- --- ---
pts Group A #5       #14    --- --- --- --- --- --- --- --- --- --- --- ---
pts Group A #7       #14    --- --- --- --- --- --- --- --- --- --- --- ---
pts group A #8       #13    --- --- --- --- --- --- --- --- --- --- --- ---
pts Group A #9       #28    --- --- --- --- --- --- --- --- --- --- --- ---
pts group A #2       >#1>     -- --- --- --- --- --- --- --- --- --- ---
pts group A #4       #13    --- --- --- --- --- --- --- --- --- --- --- ---
pts Group A #10      #13    --- --- --- --- --- --- --- --- --- --- --- ---
pts Group A #3       #14    --- --- --- --- --- --- --- --- --- --- --- ---
pts group A #1       #14    --- --- --- --- --- --- --- --- --- --- --- ---
pts Group A #11      #14    --- --- --- --- --- --- --- --- --- --- --- ---
                     #181   AAT GCA GTA GAA AGC TTA GGT GAA GAA GCA GCA GCC
                            Asn Ala Val Glu Ser Leu Gly Glu Glu Ala Ala Ala
                                Forward Primer ->
```

Figure 1B

```
pts BHGAS OU      #217   --- --- --- --- --- --- --- --- --- --- --- ---
pts group A #6    #49    --- --- --- --- --- --- --- --- --- --- --- ---
pts Group A #5    #50    --- --- --- --- --- --- --- --- --- --- --- ---
pts Group A #7    #50    --- --- --- --- --- --- --- --- --- --- --- ---
pts group A #8    #49    --- --- --- --- --- --- --- --- --- --- --- ---
pts Group A #9    #64    --- --- --- --- --- --- --- --- --- --- --- ---
pts group A #2    #33    --- --- --- --- --- --- --- --- --- --- --- ---
pts group A #4    #49    --- --- --- --- --- --- --- --- --- --- --- ---
pts Group A #10   #49    --- --- --- --- --- --A --- --- --- --- --- ---
pts Group A #3    #50    --- --- --- --- --- --A --- --- --- --- --- ---
pts group A #1    #50    --- --- --- --- --- --- --- --- --- --- --- ---
pts Group A #11   #50    --- --- --- --- --- --- --- --- --- --- --- ---
                  #217   GTT TTT GAT GCC CAT TTG ATG GTT CTT GCT GAT CCA
                         Val Phe Asp Ala His Leu MET Val Leu Ala Asp Pro

pts BHGAS OU      #253   --- --- --- --- --- --- --- --- --- --- --- ---
pts group A #6    #85    --- --- --- --- --- --- --- --- --- --- --- ---
pts Group A #5    #86    --- --- --- --- --- --- --- --- --- --- --- ---
pts Group A #7    #86    --- --- --- --- --- --- --- --- --- --- --- ---
pts group A #8    #85    --- --- --- --- --- --- --- --- --- --- --- ---
pts Group A #9    #100   --- --- --- --- --- --- --- --- --- --- --- ---
pts group A #2    #69    --- --- --T --- --- --- --- --- --- --- --- ---
pts group A #4    #85    --- --- --T --- --- --- --- --- --- --- --- ---
pts Group A #10   #85    --- --- --- --- --- --- --- --- --- --- --- ---
pts Group A #3    #86    --- --- --- --- --- --- --- --- --- --- --- ---
pts group A #1    #86    --- --- --- --- --- --- --- --- --- --- --- ---
pts Group A #11   #86    --- --- --- --- --- --- --- --- --- --- --- ---
                  #253   GAA ATG ATC AGC CAG GTT AAA GAA ACG ATT CGC GCA
                         Glu MET Ile Ser Gln Val Lys Glu Thr Ile Arg Ala
                    Fluorescein probe  Red-640 Probe

pts BHGAS OU      #289   --- --- --- --- --- --- --- --- --- --- --- ---
pts group A #6    #121   --- --- --- --- --- --- --- --- --- --- --- ---
pts Group A #5    #122   --- --- --- --- --- --- --- --- --- --- --- ---
pts Group A #7    #122   --- --- --- --- --- --- --- --- --- --- --- ---
pts group A #8    #121   --- --- --- --- --- --- --- --- --- --- --- ---
pts Group A #9    #136   --- --- --- --- --- --- --- --- --- --- --- ---
pts group A #2    #105   --- --- --- --- --- --- --- --- --- --- --- ---
pts group A #4    #121   --- --- --- --- --- --- --- --- --- --- --- ---
pts Group A #10   #121   --- --- --- --- --- --- --- --- --- --- --- ---
pts Group A #3    #122   --- --- --- --- --- --- --- --- --- --- --- ---
pts group A #1    #122   --- --- --- --- --- --- --- --- --- --- --- ---
pts Group A #11   #122   --- --- --- --- --- --- --- --- --- --- --- ---
                  #289   AAA CAA ACG AAT GCA GAA ACA GGT CTT AAA GAA GTG
                         Lys Gln Thr Asn Ala Glu Thr Gly Leu Lys Glu Val

pts BHGAS OU      #325   --- --- --- --- --- --- --- --- --- --- --- ---
pts group A #6    #157   --- --- --- --- --- --- --- --- --- --- --- ---
pts Group A #5    #158   --- --- --- --- --- --- --- --- --- --- --- ---
pts Group A #7    #158   --- --- --- --- --- --- --- --- --- --- --- ---
pts group A #8    #157   --- --- --- --- --- --- --- --- --- --- --- ---
pts Group A #9    #172   --- --- --- --- --- --- --- --- --- --- --- ---
pts group A #2    #141   --- --- --- --- --- --- --- --- --- --- --- ---
pts group A #4    #157   --- --- --- --- --- --- --- --- --- --- --- ---
pts Group A #10   #157   --- --- --- --- --- --- --- --- --- --- --- ---
pts Group A #3    #158   --- --- --- --- --- --- --- --- --- --- --- ---
pts group A #1    #158   --- --- --- --- --- --- --- --- --- --- --- ---
pts Group A #11   #158   --- --- --- --- --- --- --- --- --- --- --- ---
                  #325   ACT GAC ATG TTC ATC ACC ATC TTT GAA GGC ATG GAA
                         Thr Asp MET Phe Ile Thr Ile Phe Glu Gly MET Glu
```

Figure 1C

```
pts BHGAS OU       #361   --- --- --- --- --- --- --- --- --- --- --- ---
pts group A #6     #193   --- --- --- --- --- --- --- --- --- --- --- ---
pts Group A #5     #194   --- --- --- --- --- --- --- --- --- --- --- ---
pts Group A #7     #194   --- --- --- --- --- --- --- --- --- --- --- ---
pts group A #8     #193   --- --- --- --- --- --- --- --C --- --- --- ---
pts Group A #9     #208   --- --- --- --- --- --- --- --C --- --- --- ---
pts group A #2     #177   --- --- --- --- --- --- --- --- --- --- --- --T
pts group A #4     #193   --- --- --- --- --- --- --- --- --- --- --- --T
pts Group A #10    #193   --- --- --- --- --- --- --- --- --- --- --- ---
pts Group A #3     #194   --- --- --- --- --- --- --- --- --- --- --- ---
pts group A #1     #194   --- --- --- --- --- --- --- --- --- --- --- ---
pts Group A #11    #194   --- --- --- --- --- --- --- --C --- --- --- ---
                   #361   GAT AAC CCA TAC ATG CAA GAA CGT GCA GCG GAC ATC
                          Asp Asn Pro Tyr MET Gln Glu Arg Ala Ala Asp Ile
                          <-  Reverse Primer

pts BHGAS OU       #397   --- --- --- --- --- --- --- --- --- --- --- ---
pts group A #6     #229   --- --- --- --- --- --- --- --- --- --- --- ---
pts Group A #5     #230   --- --- --- --- --- --- --- --- --- --- --- ---
pts Group A #7     #230   --- --- --- --- --- --- --- --- --- --- --- ---
pts group A #8     #229   --- --- --- --- --- --- --- --- --- --- --- ---
pts Group A #9     #244   --- --- --- --- --- --- --- --- --- --- --- ---
pts group A #2     #213   --- --- --- --- --- --- --- --- --- --- --- ---
pts group A #4     #229   --- --- --- --- --- --- --- --- --- --- --- ---
pts Group A #10    #229   --- --- --- --- --G --- --- --- --- --- --- ---
pts Group A #3     #230   --- --- --- --- --G --- --- --- --- --- --- ---
pts group A #1     #230   --- --- --- --- --- --- --- --- --- --- --- ---
pts Group A #11    #230   --- --- --- --- --- --- --- --- --- --- --- ---
                   #397   CGC GAC GTT GCA AAA CGT GTG TTG GCT CAC CTT TTA
                          Arg Asp Val Ala Lys Arg Val Leu Ala His Leu Leu

pts BHGAS OU       #433   --- --- --- --- --- --- --- --- --- --- --- ---
pts group A #6     #265   --- --- --- --- --- --- --- --- --- --- --- ---
pts Group A #5     #266   --- --- --- --- --- --- --- --- --- --- --- ---
pts Group A #7     #266   --- --- --- --- --- --- --- --- --- --- --- ---
pts group A #8     #265   --- --- --- --- --- --- --- --- --- --- --- ---
pts Group A #9     #280   --- --- --- --- --- --- --- --- --- --- --- ---
pts group A #2     #249   --- --- --- --- --- --- --- --- --- --- --- ---
pts group A #4     #265   --- --- --- --- --- --- --- --- --- --- --- ---
pts Group A #10    #265   --- --- --- --- --- --- --- --- --- --- --- ---
pts Group A #3     #266   --- --- --- --- --- --- --- --- --- --- --- ---
pts group A #1     #266   --- --- --- --- --- --- --- --- --- --- --- ---
pts Group A #11    #266   --- --- --- --- --- --- --- --- --- --- --- ---
                   #433   GGT GTA AAA CTT CCA AAT CCA GCT ACA ATC AAT GAA
                          Gly Val Lys Leu Pro Asn Pro Ala Thr Ile Asn Glu

pts BHGAS OU       #469   --- --- --- --- --- --- --- --- --- --- --- ---
pts group A #6     #301   --- --- --- --- --- --- --- --- --- --- --- ---
pts Group A #5     #302   --- --- --- --- --- --- --- --- --- --- --- ---
pts Group A #7     #302   --- --- --- --- --- --- --- --- --- --- --- ---
pts group A #8     #301   --- --- --- --- --- --- --- --- --- --- --- ---
pts Group A #9     #316   --- --- --- --- --- --- --- --- --- --- --- ---
pts group A #2     #285   --- --- --- --- --- --- --- --- --- --- --- ---
pts group A #4     #301   --- --C --- --- --- --- --- --- --- --- --- ---
pts Group A #10    #301   --- --- --- --- --- --- --- --- --- --- --- ---
pts Group A #3     #302   --- --- --- --- --- --- --- --- --- --- --- ---
pts group A #1     #302   --- --- --- --- --- --- --- --- --- --- --- ---
pts Group A #11    #302   --- --- --- --- --- --- --- --- --- --- --- ---
                   #469   GAA TCA ATC GTT ATC GCA CAC GAT TTG ACA CCT TCA
                          Glu Ser Ile Val Ile Ala His Asp Leu Thr Pro Ser
```

Figure 1D

```
pts BHGAS OU      #505   --- --- --- --- --- --- --- --- --- --- --- ---
pts group A #6    #337   --- --- --- --- --- --- --- --- --- --- --- ---
pts Group A #5    #338   --- --- --- --- --- --- --- --- --- --- --- ---
pts Group A #7    #338   --- --- --- --- --- --- --- --- --- --- --- ---
pts group A #8    #337   --- --- --- --- --- --- --- --- --- --- --- ---
pts Group A #9    #352   --- --- --- --- --- --- --- --- --- --- --- ---
pts group A #2    #321   --- --- --- --- --- --- --- --- --- --- --- ---
pts group A #4    #337   --- --- --- --- --- --- --- --- --- --- --- ---
pts Group A #10   #337   --- --- --- --- --- --- --- --- --- --- --- ---
pts Group A #3    #338   --- --- --- --- --- --- --- --- --- --- --- ---
pts group A #1    #338   --- --- --- --- --- --- --- --- --- --- --- ---
pts Group A #11   #338   --- --- --- --- --- --- --- --- --- --- --- ---
                  #505   GAT ACT GCT CAA CTT AAC AAA CAA TTT GTA AAA GCA
                         Asp Thr Ala Gln Leu Asn Lys Gln Phe Val Lys Ala

pts BHGAS OU      #541   --- --- --- --- --- --- --- --- --- --- --- ---
pts group A #6    #373   --- --- --- --- --- --- --- --- --- --- --- ---
pts Group A #5    #374   --- --- --- --- --- --- --- --- --- --- --- ---
pts Group A #7    #374   --- --- --- --- --- --- --- --- --- --- --- ---
pts group A #8    #373   --- --- --- --- --- --- --- --- --- --- --- ---
pts Group A #9    #388   --- --- --- --- --- --- --- --- --- --- --- ---
pts group A #2    #357   --- --- --- --- --- --- --- --- --- --- --- ---
pts group A #4    #373   --- --- --- --- --- --- --- --- --- --- --- ---
pts Group A #10   #373   --- --- --- --- --- --- --- --- --- --- --- ---
pts Group A #3    #374   --- --- --- --- --- --- --- --- --- --- --- ---
pts group A #1    #374   --- --- --- --- --- --- --- --- --- --- --- ---
pts Group A #11   #374   --- --- --- --- --- --- --- --- --- --- --- ---
                  #541   TTT GTT ACA AAT ATC GGT GGT CGT ACA AGT CAC TCA
                         Phe Val Thr Asn Ile Gly Gly Arg Thr Ser His Ser

pts BHGAS OU      #577   --- --- --- --- --- --- --- --- --- --- --- ---
pts group A #6    #409   --- --- --- --- --- --- --- --- --- --- --- ---
pts Group A #5    #410   --- --- --- --- --- --- --- --- --- --- --- ---
pts Group A #7    #410   --- --- --- --- --- --- --- --- --- --- --- ---
pts group A #8    #409   --- --- --- --- --- --- --- --- --- --- --- ---
pts Group A #9    #424   --- --- --- --- --- --- --- --- --- --- --- ---
pts group A #2    #393   --- --- --- --- --- --- --- --- --- --- --- ---
pts group A #4    #409   --- --- --- --- --- --- --- --- --- --- --- ---
pts Group A #10   #409   --- --- --- --- --- --- --- --- --- --- --- ---
pts Group A #3    #410   --- --- --- --- --- --- --- --- --- --- --- ---
pts group A #1    #410   --- --- --- --- --- --- --- --- --- --- --- ---
pts Group A #11   #410   --- --- --- --- --- --- --- --- --- --- --- ---
                  #577   GCT ATC ATG GCA CGT ACA CTT GAG ATC GCT GCG GTA
                         Ala Ile MET Ala Arg Thr Leu Glu Ile Ala Ala Val

pts BHGAS OU      #613   --- --- --- --- --- --- --- --- --- --- --- ---
pts group A #6    #445   --- --- --- --- --- --- --- --- --- --- --- ---
pts Group A #5    #446   --- --- --- --- --- --- --- --- --- --- --- ---
pts Group A #7    #446   --- --- --- --- --- --- --- --- --- --- --- ---
pts group A #8    #445   --- --- --- --- --- --- --- --- --- --- --- ---
pts Group A #9    #460   --- --- --- --- --- --- --- --- --- --- --- ---
pts group A #2    #429   --- --- --- --- --- --- --- --- --- --- --- ---
pts group A #4    #445   --- --- --- --- --- --- --- --- --- --- --- ---
pts Group A #10   #445   --- --- --- --- --- --- --- --- --- --- --- ---
pts Group A #3    #446   --- --- --- --- --- --- --- --- --- --- --- ---
pts group A #1    #446   --- --- --- --- --- --- --- --- --- --- --- ---
pts Group A #11   #446   --- --- --- --- --- --- --- --- --- --- --- ---
                  #613   CTT GGA ACA AAT GAT ATT ACA AAA CGT GTT AAA GAT
                         Leu Gly Thr Asn Asp Ile Thr Lys Arg Val Lys Asp
```

Figure 1E

```
pts BHGAS OU        #649   --- --- --- --- --- --- --- --- --- --- --- ---
pts group A #6      #481   --- --- --- --- --- --- --- --- --- --- --- ---
pts Group A #5      #482   --- --- --- --- --- --- --- --- --- --- --- ---
pts Group A #7      #482   --- --- --- --- --- --- --- --- --- --- --- ---
pts group A #8      #481   --- --- --- --- --- --- --- --- --- --- --- ---
pts Group A #9      #496   --- --- --- --- --- --- --- --- --- --- --- ---
pts group A #2      #465   --- --- --- --- --- --- --- --- --- --- --- ---
pts group A #4      #481   --- --- --- --- --- --- --- --- --- --- --- ---
pts Group A #10     #481   --- --- --- --- --- --- --- --- --- --- --- ---
pts Group A #3      #482   --- --- --- --- --- --- --- --- --- --- --- ---
pts group A #1      #482   --- --- --- --- --- --- --- --- --- --- --- ---
pts Group A #11     #482   --- --- --- --- --- --- --- --- --- --- --- ---
                    #649   GGT GAT GTG ATT GCC GTT AAT GGT ATC ACT GGT GAA
                           Gly Asp Val Ile Ala Val Asn Gly Ile Thr Gly Glu

pts BHGAS OU        #685   --- --- --- --- --- --- --- --- --- --- --- ---
pts group A #6      #517   --- --- --- --- --- --- --- --- --- --- --- ---
pts Group A #5      #518   --- --- --- --- --- --- --- --- --- --- --- ---
pts Group A #7      #518   --- --- --- --- --- --- --- --- --- --- --- ---
pts group A #8      #517   --- --- --- --- --- --- --- --- --- --- --- ---
pts Group A #9      #532   --- --- --- --- --- --- --- --- --- --- --- ---
pts group A #2      #501   --- --- --- --- --- --- --- --- --- --- --- ---
pts group A #4      #517   --- --- --- --- --- --- --- --- --- --- --- ---
pts Group A #10     #517   --- --- --- --- --- --- --- --- --- --- --- ---
pts Group A #3      #518   --- --- --- --- --- --- --- --- --- --- --- ---
pts group A #1      #518   --- --- --- --- --- --- --- --- --- --- --- ---
pts Group A #11     #518   --- --- --- --- --- --- --G --- --- --- --- ---
                    #685   GTG ATT ATC GAT CCA AGC GAA GAT CAA GTA CTT GCT
                           Val Ile Ile Asp Pro Ser Glu Asp Gln Val Leu Ala

pts BHGAS OU        #721   --- --- --- --- --- --- --- --- --- --- --- ---
pts group A #6      #553   --- --- --- --- --- --- --- --- --- --- --- ---
pts Group A #5      #554   --- --- --- --- --- --- --- --- --- --- --- ---
pts Group A #7      #554   --- --- --- --- --- --- --- --- --- --- --- ---
pts group A #8      #553   --- --- --- --- --- --- --- --- --- --- --- ---
pts Group A #9      #568   --- --- --- --- --- --- --- --- --- --- --- ---
pts group A #2      #537   --- --- --- --- --- --- --- --- --- --- --- ---
pts group A #4      #553   --- --- --- --- --- --- --- --- --- --- --- ---
pts Group A #10     #553   --- --- --- --- --- --- --- --- --- --- --- ---
pts Group A #3      #554   --- --- --- --- --- --- --- --- --- --- --- ---
pts group A #1      #554   --- --- --- --- --- --- --- --- --- --- --- ---
pts Group A #11     #554   --- --- --- --- --- --- --- --- --- --- --- ---
                    #721   TTT AAA GAA GCT GGT GCG GCT TAT GCC AAA CAA AAA
                           Phe Lys Glu Ala Gly Ala Ala Tyr Ala Lys Gln Lys

pts BHGAS OU        #757   --- --- --- --- --- --- --- --- --- --C --- ---
pts group A #6      #589   --- --- --- --- --- --- --- --- --- --C --- ---
pts Group A #5      #590   --- --- --- --- --- --- --- --- --- --C --- ---
pts Group A #7      #590   --- --- --- --- --- --- --- --- --- --C --- ---
pts group A #8      #589   --- --- --- --- --- --- --- --- --- --- --- ---
pts Group A #9      #604   --- --- --- --- --- --- --- --- --- --- --- ---
pts group A #2      #573   --- --- --- --- --- --- --- --- --- --- --- ---
pts group A #4      #589   --- --- --- --- --- --- --- --- --- --- --- ---
pts Group A #10     #589   --- --- --- --- --- --- --- --- --- --- --- ---
pts Group A #3      #590   --- --- --- --- --- --- --- --- --- --- --- ---
pts group A #1      #590   --- --- --- --- --- --- --- --- --- --- --- ---
pts Group A #11     #590   --- --- --- --- --- --- --- --- --- --- --- ---
                    #757   GCA GAG TGG TCT CTC CTT AAA GAT GCG CAT ACT GAA
                           Ala Glu Trp Ser Leu Leu Lys Asp Ala His Thr Glu
```

Figure 1F

```
pts BHGAS OU      #793   --- --- --- --- --- --- --- --- --- --- --- ---
pts group A #6    #625   --- --- --- --- --- --- --- --- --- --- --- ---
pts Group A #5    #626   --- --- --- --- --- --- --- --- --- --- --- ---
pts Group A #7    #626   --- --- --- --- --- --- --- --- --- --- --- ---
pts group A #8    #625   --- --- --- --- --- --- --- --- --- --- --- ---
pts Group A #9    #640   --- --- --- --- --- --- --- --- --- --- --- ---
pts group A #2    #609   --- --- --- --- --- --- --- --- --- --- --- ---
pts group A #4    #625   --- --- --- --- --- --- --- --- --- --- --- ---
pts Group A #10   #625   --- --- --- --- --- --- --- --- --- --- --- ---
pts Group A #3    #626   --- --- --- --- --- --- --- --- --- --- --- ---
pts group A #1    #626   --- --- --- --- --- --- --- --- --- --- --- ---
pts Group A #11   #626   --- --- --- --- --- --- --- --- --- --- --- ---
                  #793   ACA GCT GAT GGC AAA CAC TTT GAA TTG GCT GCT AAT
                         Thr Ala Asp Gly Lys His Phe Glu Leu Ala Ala Asn

pts BHGAS OU      #829   --- --- --- --- --- --- --- --- --- --- --- ---
pts group A #6    #661   --- --- --- --- --- --- --- --- --- --- --- ---
pts Group A #5    #662   --- --- --- --- --- --- --- --- --- --- --- ---
pts Group A #7    #662   --- --- --- --- --- --- --- --- --- --- --- ---
pts group A #8    #661   --- --- --A --- --- --- --- --- --- --- --- ---
pts Group A #9    #676   --- --- --A --- --- --- --- --- --- --- --- ---
pts group A #2    #645   --- --- --- --- --- --- --- --- --- --- --- ---
pts group A #4    #661   --- --- --A --- --- --- --- --- --- --- --- -G-
pts Group A #10   #661   --- --- --- --- --- --- --- --- --- --- --- ---
pts Group A #3    #662   --- --- --- --- --- --- --- --- --- --- --- ---
pts group A #1    #662   --- --- --- --- --- --- --- --- --- --- --- ---
pts Group A #11   #662   --- --- --- --- --- --T --- --- --- --- --- ---
                  #829   ATC GGT ACG CCT AAA GAC GTT GAA GGT GTT AAT GAC
                         Ile Gly Thr Pro Lys Asp Val Glu Gly Val Asn Asp

pts BHGAS OU      #865   --- --T --- --- --- --- --- --- --- --- --- ---
pts group A #6    #697   --- --T --- --- --- --- --- --- --- --- --- ---
pts Group A #5    #698   --- --- --- --- --- --- --- --- --- --- --- ---
pts Group A #7    #698   --- --T --- --- --- --- --- --- --- --- --- ---
pts group A #8    #697   --- --- --- --- --- --- --- --- --- --- --- ---
pts Group A #9    #712   --- --- --- --- --- --- --- --- --- --- --- ---
pts group A #2    #681   --- --- --- --- --- --- --- --- --- --- --- ---
pts group A #4    #697   --- --- --- --- --- --- --- --- --- --- --- ---
pts Group A #10   #697   --- --- --- --- --- --- --- --- --- --- --- ---
pts Group A #3    #698   --- --- --- --- --- --- --- --- --- --- --- ---
pts group A #1    #698   --- --- --- --- --- --- --- --- --- --- --- ---
pts Group A #11   #698   --- --T --- --- --- --- --- --- --- --- --- ---
                  #865   AAT GGC GCT GAA GCT GTT GGC CTT TAC CGT ACT GAG
                         Asn Gly Ala Glu Ala Val Gly Leu Tyr Arg Thr Glu

pts BHGAS OU      #901   --- --- --- --- --- --- --- --- --- --- --- ---
pts group A #6    #733   --- --- --- --- --- --- --- --- --- --- --- ---
pts Group A #5    #734   --- --- --- --- --- --- --- --- --- --- --- ---
pts Group A #7    #734   --- --- --- --- --- --- --- --- --- --- --- ---
pts group A #8    #733   --- --- --- --- --- --- --- --- --- --- --- ---
pts Group A #9    #748   --- --- --- --- --- --- --- --- --- --- --- ---
pts group A #2    #717   --- --- --- --- --- --- --- --- --- --- --- ---
pts group A #4    #733   --- --- --- --- --- --- --- --- --- --- --- ---
pts Group A #10   #733   --- --- --- --- --- --- --- --- --- --- --- ---
pts Group A #3    #734   --- --- --- --- --- --- --- --- --- --- --- ---
pts group A #1    #734   --- --- --- --- --- --- --- --- --- --- --- ---
pts Group A #11   #734   --- --- --- --- --- --- --- --- --- --- --- ---
                  #901   TTC TTG TAC ATG GAT TCT CAA GAC TTC CCA ACT GAA
                         Phe Leu Tyr MET Asp Ser Gln Asp Phe Pro Thr Glu
```

Figure 1G

| | | | | | | | | | | | | | |
|---|---|---|---|---|---|---|---|---|---|---|---|---|---|
| pts BHGAS OU | #937 | --- | --- | --- | --- | --- | --- | --- | --- | --- | --- | --- | --- |
| pts group A #6 | #769 | --- | --- | --- | --- | --- | --- | --- | --- | --- | --- | --- | --- |
| pts Group A #5 | #770 | --- | --- | --- | --- | --- | --- | --- | --A | --- | --- | --- | --- |
| pts Group A #7 | #770 | --- | --- | --- | --- | --- | --- | --- | --- | --- | --- | --- | --- |
| pts group A #8 | #769 | --- | --- | --- | --- | --- | --- | --- | --- | --- | --- | --- | --- |
| pts Group A #9 | #784 | --- | --- | --- | --- | --- | --- | --- | --- | --- | --- | --- | --- |
| pts group A #2 | #753 | --- | --- | --- | --- | --- | --- | --- | --- | --- | --- | --- | --- |
| pts group A #4 | #769 | --- | --- | --- | --- | --- | --- | --- | --- | --- | --- | --- | --- |
| pts Group A #10 | #769 | --- | --- | --- | --- | --- | --- | --- | --- | --- | --- | --- | --- |
| pts Group A #3 | #770 | --- | --- | --- | --- | --- | --- | --- | --- | --- | --- | --- | --- |
| pts group A #1 | #770 | --- | --- | --- | --- | --- | --- | --- | --- | --- | --- | --- | --- |
| pts Group A #11 | #770 | --- | --- | --- | --- | --- | --- | --- | --- | --- | --- | --- | --- |
| | #937 | GAC | GAA | CAA | TAC | GAA | GCT | TAC | AAG | GCA | GTG | CTT | GAA |
| | | Asp | Glu | Gln | Tyr | Glu | Ala | Tyr | Lys | Ala | Val | Leu | Glu |

| | | | | | | | | | | | | | |
|---|---|---|---|---|---|---|---|---|---|---|---|---|---|
| pts BHGAS OU | #973 | --- | --- | --- | --- | --- | --- | --- | --- | --- | --- | --- | --- |
| pts group A #6 | #805 | --- | --- | --- | --- | --- | --- | --- | --- | --- | --- | --- | --- |
| pts Group A #5 | #806 | --- | --- | --- | --- | --- | --- | --- | --- | --- | --- | --A | --- |
| pts Group A #7 | #806 | --- | --- | --- | --- | --- | --- | --- | --- | --- | --- | --- | --- |
| pts group A #8 | #805 | --- | --- | --- | --- | --- | --- | --- | --- | --- | --- | --- | --- |
| pts Group A #9 | #820 | --- | --- | --- | --- | --- | --- | --- | --- | --- | --- | --- | --- |
| pts group A #2 | #789 | --- | --- | --- | --- | --- | --- | --C | --- | --- | --- | --- | --- |
| pts group A #4 | #805 | --- | --- | --- | --- | --- | --- | --- | --- | --- | --- | --- | --- |
| pts Group A #10 | #805 | --- | --- | --- | --- | --- | --- | --- | --- | --- | --- | --- | --- |
| pts Group A #3 | #806 | --- | --- | --- | --- | --- | --- | --- | --- | --- | --- | --- | --- |
| pts group A #1 | #806 | --- | --- | --- | --- | --- | --- | --- | --- | --- | --- | --A | --- |
| pts Group A #11 | #806 | --- | --- | --- | --- | --- | --- | --- | --- | --- | --- | --A | --- |
| | #973 | GGC | ATG | AAT | GGC | AAA | CCT | GTT | GTG | GTT | CGT | ACG | ATG |
| | | Gly | MET | Asn | Gly | Lys | Pro | Val | Val | Val | Arg | Thr | MET |

| | | | | | | | | | | | | | |
|---|---|---|---|---|---|---|---|---|---|---|---|---|---|
| pts BHGAS OU | #1009 | --- | --- | --- | --- | --- | --- | --- | --- | --- | --- | --- | --- |
| pts group A #6 | #841 | --- | --- | --- | --- | --- | --- | --- | --- | --- | --- | --- | --- |
| pts Group A #5 | #842 | --- | --- | --- | --A | --T | --- | --- | --- | --- | --- | --- | --- |
| pts Group A #7 | #842 | --- | --- | --- | --- | --- | --- | --- | --- | --- | --- | --- | --- |
| pts group A #8 | #841 | --- | --- | --- | --- | --- | --- | --- | --- | --- | --- | --- | --- |
| pts Group A #9 | #856 | --- | --- | --- | --- | --- | --- | --- | --- | --- | --- | --- | --- |
| pts group A #2 | #825 | --- | --- | --- | --- | --- | --- | --- | --- | --- | --- | --- | --- |
| pts group A #4 | #841 | --- | --- | --- | --- | --- | --- | --- | --- | --- | --- | --- | --- |
| pts Group A #10 | #841 | --- | --- | --- | --- | --- | --- | --- | --- | --- | --- | --- | --- |
| pts Group A #3 | #842 | --- | --- | --- | --- | --- | --- | --- | --- | --- | --- | --- | --- |
| pts group A #1 | #842 | --- | --- | --- | --A | --T | --- | --- | --- | --- | --- | --- | --- |
| pts Group A #11 | #842 | --- | --- | --- | --A | --T | --- | --- | --- | --- | --- | --- | --- |
| | #1009 | GAT | ATT | GGT | GGC | GAC | AAG | GAA | CTT | CCT | TAC | TTT | GAC |
| | | Asp | Ile | Gly | Gly | Asp | Lys | Glu | Leu | Pro | Tyr | Phe | Asp |

| | | | | | | | | | | | | | |
|---|---|---|---|---|---|---|---|---|---|---|---|---|---|
| pts BHGAS OU | #1045 | --- | --- | --- | --- | --- | --- | --- | --- | --- | --- | --- | --- |
| pts group A #6 | #877 | --- | --- | --- | --- | --- | --- | --- | --- | --- | --- | --- | --- |
| pts Group A #5 | #878 | --- | --- | --- | --- | --- | --- | --- | --- | --- | --- | --- | --- |
| pts Group A #7 | #878 | --- | --- | --- | --- | --- | --- | --- | --- | --- | --- | --- | --- |
| pts group A #8 | #877 | --- | --- | --- | --- | --- | --- | --- | --- | --- | --- | --- | --- |
| pts Group A #9 | #892 | --- | --- | --- | --- | --- | --- | --- | --- | --- | --- | --- | --- |
| pts group A #2 | #861 | --- | --- | --- | --- | --- | --- | --- | --- | --- | --- | --- | --- |
| pts group A #4 | #877 | --- | --- | --- | --- | --- | --- | --- | --- | --- | --- | --- | --- |
| pts Group A #10 | #877 | --- | --- | --- | --- | --- | --- | --- | --- | --- | --- | --- | --- |
| pts Group A #3 | #878 | --- | --- | --- | --- | --- | --- | --- | --- | --- | --- | --- | --- |
| pts group A #1 | #878 | --- | --- | --- | --- | --- | --C | --- | --- | --C | --- | --- | --- |
| pts Group A #11 | #878 | --- | --- | --- | --- | --- | --C | --- | --- | --C | --- | --- | --- |
| | #1045 | CTT | CCA | AAA | GAA | ATG | AAT | CCA | TTC | CTT | GGT | TTC | CGT |
| | | Leu | Pro | Lys | Glu | MET | Asn | Pro | Phe | Leu | Gly | Phe | Arg |

Figure 1H

```
pts BHGAS OU      #1081  --- --- --- --- --- --- --- --- --- --- --- ---
pts group A #6    #913   --- --- --- --- --- --- --- --- --- --- --- ---
pts Group A #5    #914   --- --- --- --- --- --- --- --- --- --- --- ---
pts Group A #7    #914   --- --- --- --- --- --- --- --- --- --- --C ---
pts group A #8    #913   --- --- --- --- --- --- --- --- --- --- --- ---
pts Group A #9    #928   --- --- --- --- --- --- --- --- --- --- --- ---
pts group A #2    #897   --- --- --- --- --- --- --- --- --- --- --- ---
pts group A #4    #913   --- --- --- --- --- --- --- --- --- --- --- ---
pts Group A #10   #913   --- --- --- --- --- --- --- --- --- --- --- ---
pts Group A #3    #914   --- --- --- --- --- --- --- --- --- --- --- ---
pts group A #1    #914   --- --- --- --C --A --- --- --- --- --- --- ---
pts Group A #11   #914   --- --- --- --C --A --- --- --- --- --- --- ---
                  #1081  GCT CTT CGT ATT TCC ATC TCT GAA ACT GGG GAT GCC
                         Ala Leu Arg Ile Ser Ile Ser Glu Thr Gly Asp Ala

pts BHGAS OU      #1117  --- --- --- --- --- --- --- --- --- --- --- ---
pts group A #6    #949   --- --- --- --- --- --- --- --- --- --- --- ---
pts Group A #5    #950   --- --- --- --- --- --- --- --- --- --- --C ---
pts Group A #7    #950   --- --- --- --- --- --A --- --- --- --- --- ---
pts group A #8    #949   --- --- --- --- --- --- --- --- --- --- --- ---
pts Group A #9    #964   --- --- --- --- --- --- --- --- --- --- --- ---
pts group A #2    #933   --- --- --- --- --- --- --- --- --- --- --- ---
pts group A #4    #949   --- --- --- --- --- --- --- --- --- --- --- ---
pts Group A #10   #949   --- --- --- --- --- --- --- --- --- --- --- ---
pts Group A #3    #950   --- --- --- --- --- --- --- --- --- --- --- ---
pts group A #1    #950   --- --- --- --- --- --- --- --- --- --- --C ---
pts Group A #11   #950   --- --- --- --- --- --- --- --- --- --- --- ---
                  #1117  ATG TTC CGC ACA CAA ATG CGT GCG CTT CTT CGT GCC
                         MET Phe Arg Thr Gln MET Arg Ala Leu Leu Arg Ala

pts BHGAS OU      #1153  --- --- --- --- --- --- --- --- --- --- --- ---
pts group A #6    #985   --- --- --- --- --- --- --- --- --- --- --- ---
pts Group A #5    #986   --- --- --- --- --- --- --- --C --- --- --- ---
pts Group A #7    #986   --- --- --- --- --- --- --- --- --- --- --- ---
pts group A #8    #985   --- --- --- --- --- --- --- --- --- --- --- ---
pts Group A #9    #1000  --- --- --- --- --- --- --- --- --- --- --- ---
pts group A #2    #969   --- --- --- --- --- --- --- --- --- --- --- ---
pts group A #4    #985   --- --- --- --- --- --- --- --- --- --- --- ---
pts Group A #10   #985   --- --- --- --- --- --- --- --- --- --- --- ---
pts Group A #3    #986   --- --- --- --- --- --- --- --- --- --- --- ---
pts group A #1    #986   --- --- --- --- --- --- --- --C --- --- --- ---
pts Group A #11   #986   --- --- --- --- --- --- --- --C --- --- --- ---
                  #1153  TCT GTT CAC GGA CAA CTT CGT ATT ATG TTC CCA ATG
                         Ser Val His Gly Gln Leu Arg Ile MET Phe Pro MET

pts BHGAS OU      #1189  --- --G --- --- --- --- --- --- --- --- --- ---
pts group A #6    #1021  --- --G --- --- --- --- --- --- --- --- --- ---
pts Group A #5    #1022  --A --A --- --- --- --- --- --- --- --- --- ---
pts Group A #7    #1022  --- --G --- --- --- --- --- --- --- --- --- ---
pts group A #8    #1021  --- --- --- --- --- --- --- --- --- --- --- ---
pts Group A #9    #1036  --- --- --- --- --- --- --- --- --- --- --- ---
pts group A #2    #1005  --- --G --- --- --- --- --- --- --- --- --- ---
pts group A #4    #1021  --- --- --- --- --- --- --- --- --- --- --- ---
pts Group A #10   #1021  --- --- --- --- --- --- --- --- --- --- --- ---
pts Group A #3    #1022  --- --- --- --- --- --- --- --- --- --- --- ---
pts group A #1    #1022  --A --A --- --- --- --- --- --- --- --- --- ---
pts Group A #11   #1022  --A --A --- --- --- --- --- --- --- --- --- ---
                  #1189  GTT GCC CTT CTT AAA GAA TTC CGT GCT GCA AAA GCA
                         Val Ala Leu Leu Lys Glu Phe Arg Ala Ala Lys Ala
```

Figure 1I

```
pts BHGAS OU      #1225   --- --- --C --- --- --- --- --- --- --- --- ---
pts group A #6    #1057   --- --- --C --- --- --- --- --- --- --- --- ---
pts Group A #5    #1058   A-- --- --- --- --- --- --- --- --- --- --- ---
pts Group A #7    #1058   --- --- --- --- --- --- --- --- --- --- --- ---
pts group A #8    #1057   --- --- --- --- --- --- --- --- --- --- --- ---
pts Group A #9    #1072   --- --- --- --- --- --- --- --- --- --- --- ---
pts group A #2    #1041   A-- --- --- --- --- --- --- --- --- --- --- ---
pts group A #4    #1057   --- --- --- --- --- --- --- --- --- --- --- ---
pts Group A #10   #1057   A-- --- --- --- --- --- --- --- --- --- --- ---
pts Group A #3    #1058   A-- --- --- --- --- --- --- --- --- --- --- ---
pts group A #1    #1058   --- --- --C --- --- --- --- --- --- --- --- ---
pts Group A #11   #1058   --- --- --C --- --- --- --- --- --- --- --- ---
                  #1225   GTC TTT GAT GAA GAA AAA GCA AAC TTG CTT GCA GAA
                          Val Phe Asp Glu Glu Lys Ala Asn Leu Leu Ala Glu

pts BHGAS OU      #1261   --- --- --- --- --- --- --- --- --- --- --- ---
pts group A #6    #1093   --- --- --- --- --- --- --- --- --- --- --- ---
pts Group A #5    #1094   --- --- --- --- --- --- --- --- --- --- --- ---
pts Group A #7    #1094   --- --- --- --- --- --- --- --- --- --- --- ---
pts group A #8    #1093   --- --- --- --- --- --- --- --- --- --- --- ---
pts Group A #9    #1108   --- --- --- --- --- --- --- --- --- --- --- ---
pts group A #2    #1077   --- --- --- --- --- --- --- --T --- --- --- ---
pts group A #4    #1093   --- --- --- --- --- --- --- --- --- --- --- ---
pts Group A #10   #1093   --- --- --- --- --- --- --- --- --- --- --- ---
pts Group A #3    #1094   --- --- --- --- --- --- --- --- --- --- --- ---
pts group A #1    #1094   --- --- --- --- --- --- --- --- --- --- --- ---
pts Group A #11   #1094   --- --- --- --- --- --- --- --- --- --- --- ---
                  #1261   GGC GTT GCG GTT GCT GAT GAC ATC CAA GTT GGT ATC
                          Gly Val Ala Val Ala Asp Asp Ile Gln Val Gly Ile

pts BHGAS OU      #1297   --- --- --- --- --- --- --- --- --- --- --- ---
pts group A #6    #1129   --- --- --- --- --- --- --- --- --- --- --- ---
pts Group A #5    #1130   --- --- --- --- --- --- --- --- --- --- --- ---
pts Group A #7    #1130   --- --- --- --- --- --- --- --- --- --- --- ---
pts group A #8    #1129   --- --- --- --- --- --- --- --- --- --- --- ---
pts Group A #9    #1144   --- --- --- --- --- --- --- --- --- --- --- ---
pts group A #2    #1113   --- --- --- --- --- --- --- --- --- --- --- ---
pts group A #4    #1129   --- --- --- --- --- --- --- --- --- --- --- ---
pts Group A #10   #1129   --- --- --- --- --- --- --- --- --- --- --- ---
pts Group A #3    #1130   --- --- --- --- --- --- --- --- --- --- --- ---
pts group A #1    #1130   --- --- --- --- --- --- --- --- --- --- --- ---
pts Group A #11   #1130   --- --- --- --- --- --- --- --- --- --- --- ---
                  #1297   ATG ATT GAG ATT CCT GCA GCT GCT ATG CTT GCA GAC
                          MET Ile Glu Ile Pro Ala Ala Ala MET Leu Ala Asp

pts BHGAS OU      #1333   --- --- --- --- --- --- --- --- --- --- --- ---
pts group A #6    #1165   --- --- --- --- --- --- --- --- --- --- --- ---
pts Group A #5    #1166   --- --- --- --- --- --- --- --- --- --- --- ---
pts Group A #7    #1166   --- --- --- --- --- --- --- --- --- --- --- ---
pts group A #8    #1165   --- --- --- --- --- --- --- --- --- --- --- ---
pts Group A #9    #1180   --- --- --- --- --- --- --- --- --- --- --- ---
pts group A #2    #1149   --- --- --- --- --- --- --- --- --- --- --- ---
pts group A #4    #1165   --- --- --- --- --- --- --- --- --- --- --- ---
pts Group A #10   #1165   --- --- --- --- --- --- --- --- --- --- --- ---
pts Group A #3    #1166   --- --- --- --- --- --- --- --- --- --- --- ---
pts group A #1    #1166   --- --- --- --- --- --- --- --- --- --- --- ---
pts Group A #11   #1166   --- --- --- --- --- --- --- --- --- --- --- ---
                  #1333   CAA TTT GCT AAG GAA GTT GAT TTC TTC TCA ATT GGA
                          Gln Phe Ala Lys Glu Val Asp Phe Phe Ser Ile Gly
```

Figure 1J

| | | | | | | | | | | | | | |
|---|---|---|---|---|---|---|---|---|---|---|---|---|---|
| pts BHGAS OU | #1369 | --- | --- | --- | --- | --- | --- | --- | --- | --- | --- | --- | --- |
| pts group A #6 | #1201 | --- | --- | --- | --- | --- | --- | --- | --- | --- | --- | --- | --- |
| pts Group A #5 | #1202 | --- | --- | --- | --- | --- | --- | --- | --- | --- | --- | --- | --- |
| pts Group A #7 | #1202 | --- | --- | --- | --- | --- | --- | --- | --- | --- | --- | --- | --- |
| pts group A #8 | #1201 | --- | --- | --- | --- | --- | --- | --- | --- | --- | --- | --- | --- |
| pts Group A #9 | #1216 | --- | --- | --- | --- | --- | --- | --- | --- | --- | --- | --- | --- |
| pts group A #2 | #1185 | --- | --- | --- | --- | --- | --- | --- | --- | --- | --- | --- | --- |
| pts group A #4 | #1201 | --- | --- | --- | --- | --- | --- | --- | --- | --- | --- | --- | --- |
| pts Group A #10 | #1201 | --- | --- | --- | --- | --- | --- | --- | --- | --- | --- | --- | --T |
| pts Group A #3 | #1202 | --- | --- | --- | --- | --- | --- | --- | --- | --- | --- | --- | --T |
| pts group A #1 | #1202 | --- | --- | --- | --- | --- | --- | --- | --- | --- | --- | --- | --- |
| pts Group A #11 | #1202 | --- | --- | --- | --- | --- | --- | --- | --- | --- | --- | --- | --- |
| | #1369 | ACA | AAC | GAC | CTT | ATC | CAA | TAC | ACT | ATG | GCA | GCA | GAC |
| | | Thr | Asn | Asp | Leu | Ile | Gln | Tyr | Thr | MET | Ala | Ala | Asp |

| | | | | | | | | | | | | | |
|---|---|---|---|---|---|---|---|---|---|---|---|---|---|
| pts BHGAS OU | #1405 | --- | --- | --- | --- | --- | --- | --- | --- | --- | --- | --- | --- |
| pts group A #6 | #1237 | --- | --- | --- | --- | --- | --- | --- | --- | --- | --- | --- | --- |
| pts Group A #5 | #1238 | --- | --- | --- | --- | --- | --- | --- | --- | --- | --- | --- | --- |
| pts Group A #7 | #1238 | --- | --- | --- | --- | --- | --- | --- | --- | --- | --- | --- | --- |
| pts group A #8 | #1237 | --- | --- | --- | --- | --- | --- | --- | --- | --- | --- | --- | --- |
| pts Group A #9 | #1252 | --- | --- | --- | --- | --- | --- | --- | --- | --- | --- | --- | --- |
| pts group A #2 | #1221 | --- | --- | --- | --- | --- | --- | --- | --- | --- | --- | --- | --- |
| pts group A #4 | #1237 | --- | --- | --- | --- | --- | --- | --- | --- | --- | --- | --- | --- |
| pts Group A #10 | #1237 | --- | --- | --- | --- | --- | --- | --- | --- | --- | --- | --- | --- |
| pts Group A #3 | #1238 | --- | --- | --- | --- | --- | --- | --- | --- | --- | --- | --- | --- |
| pts group A #1 | #1238 | --- | --- | --- | --- | --- | --- | --- | --- | --- | --- | --- | --- |
| pts Group A #11 | #1238 | --- | --- | --- | --- | --- | --- | --- | --- | --- | --- | --- | --- |
| | #1405 | CGT | ATG | AAC | GAA | CAA | GTA | TCA | TAC | CTT | TAC | CAA | CCA |
| | | Arg | MET | Asn | Glu | Gln | Val | Ser | Tyr | Leu | Tyr | Gln | Pro |

| | | | | | | | | | | | | | |
|---|---|---|---|---|---|---|---|---|---|---|---|---|---|
| pts BHGAS OU | #1441 | --- | --- | --- | --- | --- | --- | --- | --- | --- | --- | --- | --- |
| pts group A #6 | #1273 | --- | --- | --- | --- | --- | --- | --- | --- | --- | --- | --- | --- |
| pts Group A #5 | #1274 | --- | --- | --- | --- | --- | --- | --- | --- | --- | --- | --- | --- |
| pts Group A #7 | #1274 | --- | --- | --- | --- | --- | --- | --- | --- | --- | --- | --- | --- |
| pts group A #8 | #1273 | --- | --- | --- | --- | --- | --- | --- | --- | --- | --- | --- | --- |
| pts Group A #9 | #1288 | --- | --- | --- | --- | --- | --- | --- | --- | --- | --- | --- | --- |
| pts group A #2 | #1257 | --- | --- | --- | --- | --- | --- | --- | --- | --- | --- | --- | --- |
| pts group A #4 | #1273 | --- | --- | --- | --- | --- | --- | --- | --- | --- | --- | --- | --- |
| pts Group A #10 | #1273 | --- | --- | --- | --- | --- | --- | --- | --- | --- | --- | --- | --- |
| pts Group A #3 | #1274 | --- | --- | --- | --- | --- | --- | --- | --- | --- | --- | --- | --- |
| pts group A #1 | #1274 | --- | --- | --- | --- | --- | --- | --- | --- | --- | --- | --- | --- |
| pts Group A #11 | #1274 | --- | --- | --- | --- | --- | --- | --- | --- | --- | --- | --- | --- |
| | #1441 | TAC | AAC | CCA | TCA | ATA | TTA | CGT | TTG | ATC | AAC | AAT | GTG |
| | | Tyr | Asn | Pro | Ser | Ile | Leu | Arg | Leu | Ile | Asn | Asn | Val |

| | | | | | | | | | | | | | |
|---|---|---|---|---|---|---|---|---|---|---|---|---|---|
| pts BHGAS OU | #1477 | --- | --- | --- | --- | --- | --- | --- | --- | --- | --- | --- | --- |
| pts group A #6 | #1309 | --- | --- | --- | --- | --- | --- | --- | --- | --- | --- | --- | --- |
| pts Group A #5 | #1310 | --- | --- | --- | --- | --- | --- | --- | --- | --- | --- | --- | --- |
| pts Group A #7 | #1310 | --- | --- | --- | --- | --- | --- | --- | --- | --- | --- | --- | --- |
| pts group A #8 | #1309 | --- | --- | --- | --- | --- | --- | --- | --- | --- | --- | --- | --- |
| pts Group A #9 | #1324 | --- | --- | --- | --- | --- | --- | --- | --- | --- | --- | --- | --- |
| pts group A #2 | #1293 | --- | --- | --- | --- | --- | --- | --- | --- | --- | --- | --- | --- |
| pts group A #4 | #1309 | --- | --- | --- | --- | --- | --- | --- | --- | --- | --- | --- | --- |
| pts Group A #10 | #1309 | --- | --- | --- | --- | -C- | --- | --- | --- | --- | --- | --- | --- |
| pts Group A #3 | #1310 | --- | --- | --- | --- | --- | --- | --- | --- | --- | --- | --- | --- |
| pts group A #1 | #1310 | --- | --- | --- | --- | --- | --- | --- | --- | --- | --- | --- | --- |
| pts Group A #11 | #1310 | --- | --- | --- | --- | --- | --- | --- | --- | --- | --- | --- | --- |
| | #1477 | ATC | AAA | GCA | GCG | CAC | GCT | GAA | GGT | AAA | TGG | GCA | GGT |
| | | Ile | Lys | Ala | Ala | His | Ala | Glu | Gly | Lys | Trp | Ala | Gly |

Figure 1K

```
pts BHGAS OU        #1513   --- --- --- --- --- --- --- --- --- --- --- ---
pts group A #6      #1345   --- --- --- --- --- --- --- --- --- --- --- --
pts Group A #5      #1346   --- --- --- --- --- --- --- --- --- --- --- ---
pts Group A #7      #1346   --- --- --- --- --- --- --- --- --- --- --- ---
pts group A #8      #1345   --- --- --- --- --- --- --- --- --- --- --- ---
pts Group A #9      #1360   --- --- --- --- --- --- --- --- --- --- -
pts group A #2      #1329   --- --- --- --- --- --- --- --- --- --- -
pts group A #4      #1345   --- --- --- --- --- --- --- --- --- --- --- --
pts Group A #10     #1345   --- --- --- --- --- --- --- --- --- --- --- -
pts Group A #3      #1346   --- --- --- --- --- --- --- --- --- --- --- ---
pts group A #1      #1346   --- --- --- --- --- --- --- --- --- --- --- -
pts Group A #11     #1346   --- --- --- --- --- --- --- --- --- ---
                    #1513   ATG TGT GGT GAG ATG GCA GGT GAC CAA CAA GCT GTT
                            MET Cys Gly Glu MET Ala Gly Asp Gln Gln Ala Val

pts BHGAS OU        #1549   --- --- --- --- --- --- --- --- --- --- --- ---
pts Group A #6              (SEQ ID NO:7)
pts Group A #5      #1382   --- (SEQ ID NO:8)
pts Group A #7      #1382   --- - (SEQ ID NO:9)
pts Group A #8      #1381   --- - (SEQ ID NO:10)
pts Group A #9              (SEQ ID NO:11)
pts Group A #2              (SEQ ID NO:12)
pts Group A #4              (SEQ ID NO:13)
pts Group A #10             (SEQ ID NO:14)
pts Group A #3      #1382   --- --- --- --- (SEQ ID NO:15)
pts Group A #1              (SEQ ID NO:16)
pts Group A #11             (SEQ ID NO:17)
                    #1549   CCA CTT CTT GTC GGA ATG GGC TTG GAT GAG TTT TCT
                            Pro Leu Leu Val Gly MET Gly Leu Asp Glu Phe Ser

pts BHGAS OU        #1585   --- --- --- --- --- --- --- --- --- --- --- ---
                    #1585   ATG TCA GCA ACT TCA GTA CTT CGT ACG CGT AGT TTA
                            MET Ser Ala Thr Ser Val Leu Arg Thr Arg Ser Leu

pts BHGAS OU        #1621   --- --- --- --- --- --- --- --- --- --- --- ---
                    #1621   ATG AAG AAA CTT GAC TCT GCT AAG ATG GAA GAA TAT
                            MET Lys Lys Leu Asp Ser Ala Lys MET Glu Glu Tyr

pts BHGAS OU        #1657   --- --- --- --- --- --- --- --- --- --- --- ---
                    #1657   GCA AAT CGT GCG CTT ACA GAA TGT TCA ACA GCA GAA
                            Ala Asn Arg Ala Leu Thr Glu Cys Ser Thr Ala Glu

pts BHGAS OU        #1693   --- --- --- --- --- --- --- --- --- --- --- ---
                    #1693   GAA GTT CTT GAA CTT TCT AAA GAA TAC GTT TCT GAA
                            Glu Val Leu Glu Leu Ser Lys Glu Tyr Val Ser Glu

pts BHGAS OU        #1729   --- (SEQ ID NO:5)
                    #1729   GAT (SEQ ID NO:5)
                            Asp (SEQ ID NO:6)
```

DETECTION OF GROUP A STREPTOCOCCUS

TECHNICAL FIELD

This invention relates to bacterial diagnostics, and more particularly to detection of β-hemolytic Group A Streptococcus (GAS).

BACKGROUND

*Streptococcus pyogenes* is a group A streptococcal gram-positive bacterium that is the etiological agent of several diseases in humans, including pharyngitis and/or tonsillitis, skin infections (impetigo, erysipelas, and other forms of pyoderma), acute rheumatic fever (ARF), scarlet fever (SF), poststreptococcal glomerulonephritis (PSGN), and a toxic shock-like syndrome (TSLS). On a global basis, ARF is the most common cause of pediatric heart disease. For example, it is estimated that in India, more than six million school-aged children suffer from rheumatic heart disease. In the United States, "sore throat" is the third most common reason for physician office visits and *S. pyogenes* is recovered from about 30% of children with this complaint. There are about 25–35 million cases of streptococcal pharyngitis per year in the United States, responsible for about 1–2 billion dollars per year in health care costs.

SUMMARY

The invention provides for methods of identifying group A streptococcus (GAS) in a biological sample. Primers and probes for detecting GAS are provided by the invention, as are kits containing such primers and probes. Methods of the invention can be used to rapidly identify GAS nucleic acids from specimens for diagnosis of GAS infection. Using specific primers and probes, the methods include amplifying and monitoring the development of specific amplification products using real-time PCR.

In one aspect, the invention features a method for detecting the presence or absence of Group A Streptococcus (GAS) in a biological sample from an individual. The method to detect GAS includes performing at least one cycling step, which includes an amplifying step and a hybridizing ste. The amplifying step includes contacting the sample with a pair of ptsI primers to produce a ptsI amplification product if a GAS ptsI nucleic acid molecule is present in the sample, and the hybridizing step includes contacting the sample with a pair of ptsI probes. Generally, the members of the pair of ptsI probes hybridize to the amplification product within no more than five nucleotides of each other. A first ptsI probe of the pair of ptsI probes is typically labeled with a donor fluorescent moiety and a second ptsI probe of the pair of ptsI probes is typically labeled with a corresponding acceptor fluorescent moiety. The method further includes detecting the presence or absence of fluorescence resonance energy transfer (FRET) between the donor fluorescent moiety of the first ptsI probe and the acceptor fluorescent moiety of the second ptsI probe. The presence of FRET is usually indicative of the presence of GAS in the biological sample, and the absence of FRET is usually indicative of the absence of GAS in the biological sample. The method can still further include determining the melting temperature between one or both of the ptsI probe(s) and the ptsI amplification product. The melting temperature can confirm the presence or the absence of the GAS.

A pair of ptsI primers generally includes a first ptsI primer and a second ptsI primer. The first ptsI primer can include the sequence 5'-AAA TGC AGT AGA AAG CTT AGG-3' (SEQ ID NO:1), and the second ptsI primer can include the sequence 5'-TGC ATG TAT GGG TTA TCT TCC-3' (SEQ ID NO:2). The first ptsI probe can include the sequence 5'-TTG CTG ATC CAG AAA TGA T-3' (SEQ ID NO:3), and the second ptsI probe can include the sequence 5'-AGC CAG GTT AAA GAA ACG ATT CGC-3' (SEQ ID NO:4).

The members of the pair of ptsI probes can hybridize within no more than two nucleotides of each other, or can hybridize within no more than one nucleotide of each other. A representative donor fluorescent moiety is fluorescein, and representative acceptor fluorescent moiety is selected from the group consisting of LC™-RED 640 (LightCycler™-Red 640-N-hydroxysuccinimide ester), LC™-RED 705 (LightCycler™-Red 705-Phosphoramidite), and cyanine dyes such as CY5 and CY5.5.

In one aspect, the detecting step includes exciting the biological sample at a wavelength absorbed by the donor fluorescent moiety and visualizing and/or measuring the wavelength emitted by the acceptor fluorescent moiety. In another aspect, the detecting comprises quantitating the FRET. In yet another aspect, the detecting step is performed after each cycling step, and further, can be performed in real-time.

Generally, the presence of the FRET within 50 cycles, or within 40 cycles, or within 30 cycles, indicates the presence of a GAS infection in the individual. Representative biological samples include throat swabs, tissues and bodily fluids.

The above-described methods can further include preventing amplification of a contaminant nucleic acid. Preventing amplification can include performing the amplification step in the presence of uracil and treating the biological sample with uracil-DNA glycosylase prior to a first amplification step. In addition, the ycling step can be performed on a control sample. A control sample can include the GAS ptsI nucleic acid molecule. Alternatively, such a control sample can be amplified using a pair of control primers and hybridized using a pair of control probes. The control primers and the control probes are usually other than the ptsI primers and the ptsI probes, respectively. A control amplification product is produced if control template is present in the sample, and the control probes hybridize to the control amplification product.

In another aspect of the invention, there are provided articles of manufacture, including a pair of ptsI primers; a pair of ptsI probes; and a donor fluorescent moiety and a corresponding fluorescent moiety. A pair of ptsI primers generally includes a first ptsI primer and a second ptsI primer. A first ptsI primer can include the sequence 5'-AAA TGC AGT AGA AAG CTT AGG-3' (SEQ ID NO:1), and the second ptsI primer can include the sequence 5'-TGC ATG TAT GGG TTA TCT TCC-3' (SEQ ID NO:2). A pair of ptsI probes can include a first ptsI probe and a second ptsI probe. A first ptsI probe can include the sequence 5'-TTG CTG ATC CAG AAA TGA T-3' (SEQ ID NO:3), and the second ptsI probe can include the sequence 5'-AGC CAG GTT AAA GAA ACG ATT CGC-3' (SEQ ID NO:4). The probes in such articles of manufacture can be labeled with a donor fluorescent moiety and with a corresponding acceptor fluorescent moiety. The articles of manufacture also can include a package label or package insert having instructions thereon for using the pair of ptsI primers and the pair of ptsI probes to detect the presence or absence of GAS in a biological sample.

In yet another aspect, the invention provides a method for detecting the presence or absence of GAS in a biological sample from an individual. Such a method includes performing at least one cycling step, wherein a cycling step comprises an amplifying step and a hybridizing step. An amplifying step includes contacting the sample with a pair of ptsI primers to produce a ptsI amplification product if a GAS ptsI nucleic acid molecule is present in the sample. A hybridizing step includes contacting the sample with a ptsI probe, wherein the ptsI probe is labeled with a donor fluorescent moiety and a corresponding acceptor fluorescent moiety. The method further includes detecting the presence or absence of fluorescence resonance energy transfer (FRET) between the donor fluorescent moiety and the acceptor fluorescent moiety of the ptsI probe. The presence or absence of FRET is indicative of the presence or absence of GAS in the sample. Amplification can employ a polymerase enzyme having 5' to 3' exonuclease activity, and the donor and acceptor fluorescent moieties can be within no more than 5 nucleotides of each other on the probe. In such a method, the ptsI probe can include a nucleic acid sequence that permits secondary structure formation that results in spatial proximity between the donor and the acceptor fluorescent moiety. In the above-described methods, the acceptor fluorescent moiety can be a quencher.

In another aspect, the invention provides a method for detecting the presence or absence of GAS in a biological sample from an individual. Such a method includes performing at least one cycling step, wherein a cycling step comprises an amplifying step and a dye-binding step. An amplifying step includes contacting the sample with a pair of ptsI primers to produce a ptsI amplification product if a GAS ptsI nucleic acid molecule is present in the sample. A dye-binding step comprises contacting the ptsI amplification product with a nucleic acid binding dye. The method further includes detecting the presence or absence of binding of the nucleic acid binding dye to the amplification product. The presence of binding is usually indicative of the presence of GAS in the sample, and the absence of binding is usually indicative of the absence of GAS in the sample. Representative nucleic acid binding dyes include SYBRGREENI®, SYBRGOLD®, and ethidium bromide. Such a method can further include determining the melting temperature between the ptsI amplification product and the nucleic acid binding dye. The melting temperature can confirm the presence or absence of the GAS.

Unless othehrwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In addition, the materials, methods, and examples are illustrative only and not intended to be limiting. All publications, patent applications, patents, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the drawings and detailed description, and from the claims.

DESCRIPTION OF THE DRAWINGS

FIG. 1 is an alignment of ptsI nucleic acid sequences from the Oklahoma University M1 strain (Ferretti et al., 2001, *Proc. Natl. Acad. Sci. USA*, 98:4658–63) and from 11 Group A Streptococcus (GAS) isolates. The location of the primers and probes used herein for the real-time PCR assay are shown. Dashes refer to positions in which the nucleotides are identical to the ptsI nucleic acid sequence from the Oklahoma University M1 strain.

DETAILED DESCRIPTION

A real-time PCR assay that is more sensitive than existing assays is described herein for detecting GAS in a biological sample. Primers and probes for detecting GAS infections and articles of manufacture containing such primers and probes are provided by the invention. The increased sensitivity of the real-time PCR assay for detecting GAS compared to other methods, as well as the improved features of real-time PCR including sample containment and real-time detection of the amplified product, make feasible the implementation of this technology for routine diagnosis of GAS infections in the clinical laboratory.

β-Hemolytic Group A Streptococcus (GAS)

Streptococci are Gram-positive, non-motile bacteria that are often arranged in pairs or chains. Streptococci generally exist as commensals and parasites in humans, animals, and saprophytes. Most streptococcal strains are facultative anaerobes with complex nutritional requirements. Streptococcal strains typically require blood- or serum-enriched media for growth. Streptococcal strains are oxidase-negative and catalase-negative, the latter being useful for distinguishing streptococci from staphylococci. Streptococci have a rigid cell wall with a typical Gram-positive peptidoglycan layer, an inner plasma membrane, mesosomal vesicles, and a nucleoid. The cell wall is divided by crosswall septation.

The cell wall of GAS organisms contains group- and type-specific antigens. For example, GAS organisms produce a group-specific carbohydrate (i.e., a C-polysaccharide) that is a branched polymer of L-rhamnose and N-acetyl-D-glucosamine in a 2:1 ratio. The N-acetyl-D-glucosamine is the antigenic component of the group-specific carbohydrate. The carbohydrate is linked by phosphate-containing bridges to peptidoglycans composed of N-acetyl-D-glucosamine, N-acetyl-D-muramic acid, D-glutamic acid, L-lysine, and D- and L-alanine. The GAS-specific carbohydrate generally comprises 10% of the dry weight of the cell. In addition, GAS organisms produce two major classes of type-specific proteins, the M and the T antigens (minor classes include F, R, and M-like antigens). The M proteins are fimbriae-like extensions associated with virulent strains, while the T proteins are a useful epidemiological marker that have not been associated with virulence. GAS organisms also contain a capsular polysaccharide composed of hyaluronic acid.

GAS Nucleic Acids and Oligonucleotides

A metabolic pathway chart showing the phosphoenolpyruvate:phosphotransferase system is available online. Briefly, the phosphoenolpyruvate:phosphotransferase system (pep:pts or pts) is composed of two enzymes, HPr and enzyme I (or EI) encoded by the ptsH and ptsI genes, respectively. Enzyme I is autophosphorylated by phosphoenolpyruvate. Phosphorylated EI then catalyzes the phosphorylation of HPr in the membrane. HPr phosphorylates a sugar-specific enzyme that is translocated across the membrane. Thus, EI and HPr are necessary for sugar translocation. The phosphotransferase system is reviewed by, for example, Postma et al. (1993, *Microbiol. Rev.*, 57:543–94) and the pts operon is reviewed by, for example, Vadeboncoeur et al. (2000, *J. Mol. Microbiol. Biotechnol.*, 2:483–90).

The invention provides methods to detect GAS by amplifying, for example, GAS nucleic acid molecules corresponding to aportion of the ptsI gene encoding enzyme I (EI) of the phosphoenolpyruvate:sugar phosphotransferase system. GAS nucleic acid molecules other than those exemplified herein (e.g., other than ptsI) also can be used to detect GAS in a sample and are known to those of skill in the art. Nucleic acid sequences encoding GAS ptsI have been described (see, for example, Ferretti et al., 2001, *Proc. Natl. Acad. Sci. USA*, 98:4658–63; and GenBank Accession Nos. NC 002737, and AE004092). Specifically, primers and probes to amplify and detect GAS ptsI nucleic acid molecules are provided by the invention.

Primers that amplify a GAS nucleic acid molecule, e.g., a portion of the ptsI gene, can be designed using, for example, a computer program such as OLIGO (Molecular Biology Insights Inc., Cascade, Colo.). Important features when designing oligonucleotides to be used as amplification primers include, but are not limited to, an appropriate size amplification product to facilitate detection (e.g., by electrophoresis), similar melting temperatures for the members of a pair of primers, and the length of each primer (i.e., the primers need to be long enough to anneal with sequence-specificity and to initiate synthesis but not so long that fidelity is reduced during oligonucleotide synthesis). Typically, oligonucleotide primers are 8 to 50 nucleotides in length (e.g., 10, 12, 14, 16, 18, 20, 22, 24, 26, 28, 30, 32, 34, 36, 38, 40, 42, 44, 46, 48, or 50 nucleotides in length). "ptsI primers" as used herein refers to oligonucleotide primers that specifically anneal to GAS nucleic acid sequences encoding ptsI and initiate synthesis therefrom under appropriate conditions.

Designing oligonucleotides to be used as hybridization probes can be performed in a manner similar to the design of primers, although the members of a pair of probes preferably anneal to an amplification product within no more than 5 nucleotides of each other on the same strand such that fluorescent resonance energy transfer (FRET) can occur (e.g., within no more than 1, 2, 3, or 4 nucleotides of each other). This minimal degree of separation typically brings the respective fluorescent moieties into sufficient proximity such that FRET occurs. It is to be understood, however, that other separation distances (e.g., 6 or more nucleotides) are possible provided the fluorescent moieties are appropriately positioned relative to each other (for example, with a linker arm) such that FRET can occur. In addition, probes can be designed to hybridize to targets that contain a mutation or polymorphism, thereby allowing differential detection of GAS strains based on either absolute hybridization of different pairs of probes corresponding to the particular GAS strain to be distinguished or differential melting temperatures between, for example, members of a pair of probes and each amplification product corresponding to a GAS strain to be distinguished. For example, using appropriate probe pairs, group A streptococcus (*S. pyogenes*) can be distinguished from other streptococcal strains (for example, group B streptococcus (*S. agalactiae*), group C streptococcus (e.g., *S. equisimillis*) and group G streptococcus (e.g., *S. canis*)). As with oligonucleotide primers, oligonucleotide probes usually have similar melting temperatures, and the length of each probe must be sufficient for sequence-specific hybridization to occur but not so long that fidelity is reduced during synthesis. Oligonucleotide probes are 8 to 50 nucleotides in length (e.g., 10, 12, 14, 16, 18, 20, 22, 24, 26, 28, 30, 32, 34, 36, 38, 40, 42, 44, 46, 48, or 50 nucleotides in length). "ptsI probes" as used herein refers to oligonucleotide probes that specifically anneal to a ptsI amplification product.

Constructs of the invention include vectors containing a GAS nucleic acid molecule, e.g., a GAS ptsI gene or fragment thereof. Constructs can be used, for example, as a control template nucleic acid. Vectors suitable for use in the present invention are commercially available and/or produced by recombinant DNA technology methods routine in the art. A GAS ptsI nucleic acid molecule can be obtained, for example, by chemical synthesis, direct cloning from GAS, or by PCR amplification. A GAS nucleic acid molecule or fragments thereof can be operably linked to a promoter or other regulatory element such as an enhancer sequence, a response element or an inducible element that modulates expression of the GAS nucleic acid molecule. As used herein, operably linking refers to connecting a promoter and/or other regulatory elements to a GAS nucleic acid molecule in such a way as to permit and/or regulate expression of the GAS nucleic acid molecule. A promoter that does not normally direct expression of GAS ptsI can be used to direct transcription of a ptsI nucleic acid molecule using, for example a viral polymerase, a bacterial polymerase, or a eukaryotic RNA polymerase I. Alternatively, the ptsI native promoter can be used to direct transcription of a ptsI nucleic acid molecule using, for example, an *S. pyogenes* RNA polymerase or a host RNA polymerase. In addition, operably linked can refer to an appropriate connection between a GAS ptsI promoter or other regulatory element to a heterologous coding sequence (i.e., a non-ptsI coding sequence, for example a reporter gene) in such a way as to permit expression of the heterologous coding sequence.

Constructs suitable for use in the methods of the invention typically include, in addition to a GAS ptsI nucleic acid molecule, sequences encoding a selectable marker (e.g., an antibiotic resistance gene) for selecting desired constructs and/or transformants, and an origin of replication. The choice of vector systems usually depends upon several factors, including, but not limited to, the choice of host cells, replication efficiency, selectability, inducibility, and the ease of recovery.

Constructs of the invention containing a GAS ptsI nucleic acid molecule can be propagated in a host cell. As used herein, the term host cell is meant to include prokaryotes and eukaryotes such as yeast, plant and animal cells. Prokaryotic hosts can include *E. coli, Salmonella typhimurium, Serratia marcescens* and *Bacillus subtilis*. Eukaryotic hosts include yeasts such as *S. cerevisiae, S. pombe*, and *Pichia pastoris*, mammalian cells such as COS cells or Chinese hamster ovary (CHO) cells, insect cells, and plant cells such as *Arabidopsis thaliana* and *Nicotiana tabacum*. A construct of the invention can be introduced into a host cell using any of the techniques commonly known to those of ordinary skill in the art. For example, calcium phosphate precipitation, electroporation, heat shock, lipofection, microinjection, and viral-mediated nucleic acid transfer are common methods for introducing nucleic acids into host cells. In addition, naked DNA can be delivered directly to cells (see, e.g., U.S. Pat. Nos. 5,580,859 and 5,589,466).

Polymerase Chain Reaction (PCR)

U.S. Pat. Nos. 4,683,202, 4,683,195, 4,800,159, and 4,965,188 disclose conventional PCR techniques. PCR typically employs two oligonucleotide primers that bind to a selected nucleic acid template (e.g., DNA or RNA). Primers useful in the present invention include oligonucleotides capable of acting as a point of initiation of nucleic acid synthesis within a GAS ptsI nucleic acid sequence. A primer can be purified from a restriction digest by conventional methods, or it can be produced synthetically. A primer is preferably single-stranded for maximum efficiency in amplification, but a primer can be double-stranded. Double-stranded primers are first denatured, i.e., treated to separate the strands. One method of denaturing double stranded nucleic acids is by heating.

The term "thermostable polymerase" refers to a polymerase enzyme that is heat stable, i.e., the enzyme catalyzes the formation of primer extension products complementary to a template and does not irreversibly denature when subjected to the elevated temperatures for the time necessary to effect denaturation of double-stranded template nucleic acids. Generally, the synthesis is initiated at the 3' end of each primer and proceeds in the 5' to 3' direction along the template strand. Thermostable polymerases have been isolated from *Thermus flavus, T. ruber, T. thermophilus, T. adquaticus, T. lacteus, T. rubens, Bacillus stearothermophilus*, and *Methanothermus fervidus*. Nonetheless, polymerases that are not thermostable also can be employed in PCR provided the enzyme is replenished.

If the GAS, template nucleic acid is double-stranded, it is necessary to separate the two strands before it can be used as a template in PCR. Strand separation can be accomplished by any suitable denaturing method including physical, chemical or enzymatic means. One method of separating the nucleic acid strands involves heating the nucleic acid until it is predominately denatured (e.g., greater than 50%, 60%, 70%, 80%, 90% or 95% denatured). The heating conditions necessary for denaturing template nucleic acid will depend, e.g., on the buffer salt concentration and the length and nucleotide composition of the nucleic acids being denatured, but typically range from about 90° C. to about 105° C. for a time depending on features of the reaction such as temperature and the nucleic acid length. Denaturation is typically performed for about 0 sec to 4 min.

If the double-stranded nucleic acid is denatured by heat, the reaction mixture is allowed to cool to a temperature that promotes annealing of each primer to its target sequence on the GAS nucleic acid. The temperature for annealing is usually from about 35° C. to about 65° C. The reaction mixture is then adjusted to a temperature at which the activity of the polymerase is promoted or optimized, e.g., a temperature sufficient for extension to occur from the annealed primer to generate products complementary to the template nucleic acid. The temperature should be sufficient to synthesize an extension product from each primer that is annealed to a nucleic acid template, but should not be so high as to denature an extension product from its complementary template. The temperature generally ranges from about 40° to 80° C.

PCR assays can employ GAS nucleic acid such as DNA or RNA, including messenger RNA (mRNA). The template nucleic acid need not be purified; it may be a minor fraction of a complex mixture, such as GAS nucleic acid contained in human cells. DNA or RNA may be extracted from any biological sample such as a throat swab, tissue (e.g., skin, or lymph node) or body fluids (e.g., cerebrospinal fluid (CSF), blood, or urine) by routine techniques such as those described in *Diagnostic Molecular Microbiology: Principles and Applications* (Persing et al. (eds), 1993, American Society for Microbiology, Washington D.C.). Template nucleic acids can be obtained from any number of sources, such as plasmids, or natural sources including bacteria, yeast, viruses, organelles, or higher organisms such as plants or animals.

The oligontcleotide primers are combined with other PCR reagents under reaction conditions that induce primer extension. For example, chain extension reactions generally include 50 mM KCl, 10 mM Tris-HCl (pH 8.3), 1.5 mM $MgCl_2$, 0.001% (w/v) gelatin, 0.5–1.0 μg denatured template DNA, 50 pmoles of each oligonucleotide primer, 2.5 U of Taq polymerase, and 10% DMSO. The reactions usually contain 150 to 320 μM each of dATP, dCTP, dTTP, dGTP, or one or more analogs thereof.

The newly synthesized strands form a double-stranded molecule that can be used in the succeeding steps of the reaction. The steps of strand separation, annealing, and elongation can be repeated as often as needed to produce the desired quantity amplification products corresponding to the target GAS nucleic acid molecule. The limiting factors in the reaction are the amounts of primers, thermostable enzyme, and nucleoside triphosphates present in the reaction. The cycling steps (i.e., amplification and hybridization) are preferably repeated at least once. For use in detection, the number of cycling steps will depend, e.g., on the nature of the sample. If the sample is a complex mixture of nucleic acids, more cycling steps may be required to amplify the target sequence sufficient for detection. Generally, the cycling steps are repeated at least about 20 times, but may be repeated as many as 40, 60, or even 100 times.

Fluorescent Resonance Energy Transfer (FRET)

FRET technology (see, for example, U.S. Pat. Nos. 4,996,143, 5,565,322, 5,849,489, and 6,162,603) is based on the fact that when a donor and a corresponding acceptor fluorescent moiety are positioned within a certain distance of each other, energy transfer takes place between the two fluorescent moieties that can be visualized or otherwise detected and/or quantitated. As used herein, two oligonucleotide probes, each containing a fluorescent moiety, can hybridize to an amplification product at particular positions determined by the complementarity of the oligonucleotide probes to the GAS target nucleic acid sequence. Upon hybridization of the oligonucleotide probes to the amplification product at the appropriate positions, a FRET signal is generated.

Fluorescent analysis can be carried out using, for example, a photon counting epifluorescent microscope system (containing the appropriate dichroic mirror and filters for monitoring fluorescent emission at the particular range), a photon counting photomultiplier system or a fluorometer. Excitation to initiate energy transfer can be carried out with an argon ion laser, a high intensity mercury (Hg) arc lamp, a fiber optic light source, or other high intensity light source appropriately filtered for excitation in the desired range.

As used herein with respect to donor and corresponding acceptor fluorescent moieties, "corresponding" refers to an acceptor fluorescent moiety having an emission spectrum that overlaps the excitation spectrum of the donor fluorescent moiety. The wavelength maximum of the emission spectrum of the acceptor fluorescent moiety preferably should be at least 100 nm greater than the wavelength maximum of the excitation spectrum of the donor fluorescent moiety. Accordingly, efficient non-radiative energy transfer can be produced therebetween.

Fluorescent donor and corresponding acceptor moieties are generally chosen for (a) high efficiency Förster energy transfer; (b) a large final Stokes shift (>100 nm); (c) shift of the emission as far as possible into the red portion of the visible spectrum (>600 nm); and (d) shift of the emission to a higher wavelength than the Raman water fluorescent emission produced by excitation at the donor excitation wavelength. For example, a donor fluorescent moiety can be chosen that has its excitation maximum near a laser line (for example, Helium-Cadmium 442 nm or Argon 488 nm), a high extinction coefficient, a high quantum yield, and a good overlap of its fluorescent emission with the excitation spectrum of the corresponding acceptor fluorescent moiety. A corresponding acceptor fluorescent moiety can be chosen that has a high extinction coefficient, a high quantum yield, a good overlap of its excitation with the emission of the donor fluorescent moiety, and emission in the red part of the visible spectrum (>600 nm).

Representative donor fluorescent moieties that can be used with various acceptor fluorescent moieties in FRET technology include fluorescein, Lucifer Yellow, B-pliycoerythrin, 9-acridineisothiocyanate, Lucifer Yellow VS, 4-acetamido-4'-isothio-cyanatostilbene-2,2'-disulfonic acid, 7-diethylamino-3-(4'-isothiocyanatophenyl)-4-methylcoumarin, succinimdyl 1-pyrenebutyrate, and 4-acetamido-4'-isothiocyanatostilbene-2,2'-disulfonic acid derivatives. Representative acceptor fluorescent moieties, depending upon the donor fluorescent moiety used, include LC™-RED 640 (LightCycler™-Red 640-N-hydroxysuccinimide ester), LC™-RED 705 (LightCycler™-Red 705-Phosphoramidite), cyanine dyes such as CY5 and CY5.5, Lissamine rhodamine B sulfonyl chloride, tetramethyl rhodamine isothiocyanate, rhodamine x isothiocyanate, erythrosine isothiocyanate, fluorescein, diethylenetriamine pentaacetate or other chelates of Lanthanide ions (e.g., Europium, or Terbium). Donor and acceptor fluorescent moieties can be obtained, for example, from Molecular Probes (Junction City, Oreg.) or Sigma Chemical Co. (St. Louis, Mo.).

The donor and acceptor fluorescent moieties can be attached to the appropriate probe oligonucleotide via a linker arm. The length of each linker arm can be important, as the linker arms will affect the distance between the donor and the acceptor fluorescent moieties. The length of a linker arm for the purpose of the present invention is the distance in Angstroms (Å) from the nucleotide base to the fluorescent moiety. In general, a linker arm is from about 10 to about 25 Å. The linker arm may be of the kind described in WO 84/03285. WO 84/03285 also discloses methods for attaching linker arms to particular nucleotide bases, and also for attaching fluorescent moieties to a linker arm.

An acceptor fluorescent moiety such as LC™-RED 640 (LightCycler™-Red 640-N-hydroxysuccinimide ester) can be combined with C6-Phosphoramidites (available from ABI (Foster City, Calif.) or Glen Research (Sterling, Va.)) to produce, for example, LC™-RED 640 (LightCycler™-Red 640-Phosphoramidite). Frequently used linkers to couple a donor fluorescent moiety such as fluorescein to an oligonucleotide include thiourea linkers (FITC-derived, for example, fluorescein-CPG's from Glen Research or ChemGene (Ashland, Mass.)), amide-linkers (fluorescein-NHS-ester-derived, such as fluorescein-CPG from BioGenex (San Ramon, Calif.)), or 3'-amino-CPG's that require coupling of a fluorescein-NHS-ester after oligonucleotide synthesis.

Detection of Group A Streptococcus (GAS)

Cell culture is considered the gold standard for detection of GAS. Culture, however, suffers from slow turnaround time (e.g., 1 to 2 days). There are a number of variations on the methodology of cell culture that are used for the detection of GAS. Culture of throat swabs is generally done by streaking a patient's swab on a plate containing, for example, T-soy blood agar. Following incubation, GAS is identified by the presence of β-hemolytic colonies. Culture is usually used in conjunction with an antigen test to confirm the presence of GAS. For example, β-hemolytic colonies can be tested for the presence of the group A antigen using a fluorescently labeled antibody, or a bacitracin disk can be placed on the plate. Bacitracin inhibits the growth of β-hemolytic colonies.

There are a number of rapid antigen tests on the market that use antibodies directed against, for example, the group A antigen. An analysis of the rapid antigen tests performed by nurses and technologists found sensitivities in the 50 to 60% range. A laboratory comparison using TESTPACK® PLUS™ STREP A (Abbott Laboratories, Abbott Park, Ill.; an immunoassay for detecting Group A Streptococcal antigen from throat swab specimens or for confirmation of presumptive Group A Streptococcal colonies recovered from culture) found 68% sensitivity. The rapid antigen assays currently available are not sensitive enough to replace culture, i.e., to serve as stand-alone diagnostic assays, and the Infectious Disease Society of America (IDSA) has recommended that rapid antigen tests for *S. pyogenes* be backed up with culture.

Over the past 15 years, a number of rapid test formats, frequently referred to as "rapid strep screens" (RSSs), have emerged. Generally, these assays are modifications of the immunoassay methods and include simple, single-use devices adapted for manual use. Single-use immunoassay devices are classified as moderately complex under the Clinical Laboratory Improvement Amendment (CLIA, 1988) guidelines. Because they can be performed quickly, relatively inexpensively, and require few additional reagents, they are suited to a variety of physician office testing environments. Latex agglutination is a well-established immunoassay method in which latex particles are coated with an analyte-specific capture reagent, such as an antibody. The major limitations of agglutination-based assays are their lack of sensitivity and specificity and the subjective nature of test result interpretation. However, because these tests are fast, inexpensive, and require minimal reagents, they have been widely used. Other variations of immunoassay technology are the flow-through membrane devices. Hybritech's® (San Diego, Calif.) ICON® format is based on this method and is available for the detection of a number of infectious diseases. Other flow-through membrane tests include Kodak's (Rochester, N.Y.) SURE-CELL® and Becton Dickinson's (Franklin Lakes, N.J.) QTEST®. Rapid assays such as the DIRECTIGEN™ 1-2-3 (Becton Dickinson & Co., Sparks, Md.) can also incorporate liposomes.

A second-generation immunoassay technology is available in BioStar's® (Boulder, Colo.) Strep A Optical ImmunoAssay (STREP A OIA®) test. In this test, a solid reflective support is coated with thin film selected to specifically attenuate the reflection of certain wavelengths of visible light through destructive interference, thereby producing the device's characteristic gold background color. Any change in the mass on the surface of the device due to analyte binding modifies the thin film and shifts the attenuated wavelengths, resulting in a color change from gold to purple. The OIA test requires a very small sample such that repeated or additional testing can be performed without collecting multiple specimens from the patient. STREP A OIA® assays are significantly more sensitive than first-generation rapid strep screens and studies that examined the STREP A OIA® assay compared with culture found 81–92% sensitivity of the STREP A OIA® assay. As with other rapid assays, the STREP A OIA® method has been classified as moderately complex.

The GROUP A STREPTOCOCCUS DIRECT TEST is a commercially available assay that uses nucleic acid hybridization for the qualitative detection of GAS RNA. See GenProbe Inc., San Diego, Calif. GenProbe reports that the assay has a sensitivity of 91.7% and a specificity of 99.3%. Other studies have shown the GROUP A STREPTOCOCCUS DIRECT TEST to be 86% sensitive when compared to a 72-hour cell culture assay and 93% sensitive when compared to standard culture methods that include serotyping of colonies. For most diagnostic or clinical laboratories, this level of sensitivity is not high enough to allow GROUP A STREPTOCOCCUS DIRECT TEST to replace culture.

The real-time assay described herein has been compared to cell culture and to a rapid antigen test using 500 patient specimens. The real-time PCR method is more sensitive than culture and far superior in sensitivity to the rapid antigen test. The specificity was also determined using DNA from cultures of a variety of streptococcal and non-streptococcal microorganisms commonly found in the throat and respiratory tract.

The invention provides methods for detecting the presence or absence of GAS in a biological sample from an individual. Methods provided by the invention avoid problems of sample contamination, false negatives and false positives. The methods include performing at least one cycling step that includes amplifying and hybridizing. An amplification step includes contacting the biological sample with a pair of ptsI primers to produce a ptsI amplification product if a GAS ptsI nucleic acid molecule is present in the sample. Each of the ptsI primers anneals to a target within or adjacent to a GAS ptsI nucleic acid molecule such that at least a portion of the amplification product contains nucleic acid sequence corresponding to ptsI and, more importantly, such that the amplification product contains the nucleic acid sequences that are complementary to ptsI probes. A hybridizing step includes contacting the sample with a pair of ptsI probes. Generally, the members of the pair of ptsI probes hybridize to the amplification product within no more than five nucleotides of each other. According to the invention, a first ptsI probe of the pair of ptsI probes is labeled with a donor fluorescent moiety and a second ptsI probe of the pair of ptsI probes is labeled with a corresponding acceptor fluorescent moiety. The method further includes detecting the presence of absence of FRET between the donor fluorescent moiety of the first ptsI probe and the corresponding acceptor fluorescent moiety of the second ptsI probe. Multiple cycling steps can be performed, preferably in a thermocycler. The above-described methods for detecting GAS in a biological sample using primers and probes directed toward ptsI also can be performed using other GAS gene-specific primers and probes.

As used herein, "amplifying" refers to the process of synthesizing nucleic acid molecules that are complementary to one or both strands of a template nucleic acid (e.g., ptsI GAS nucleic acid molecules). Amplifying a nucleic acid molecule typically includes denaturing the template nucleic acid, annealing primers to the template nucleic acid at a temperature that is below the melting temperatures of the primers, and enzymatically elongating from the primers to generate an amplification product. The denaturing, annealing and elongating steps each can be performed once. Generally, however, the denaturing, annealing and elongating steps are performed multiple times such that the amount of amplification product is increasing, often times exponentially, although exponential amplification is not required by the present methods. Amplification typically requires the presence of deoxyribonucleoside triphosphates, a DNA polymerase enzyme (e.g, PLATINUM® TAQ (derived from recombinant Taq DNA polymerase by binding of a thermolabile inhibitor containing monoclonal antibodies to Taq DNA polymerase such that the inhibitor is denatured during the initial denaturation step of PCR and active Taq DNA polymerase is released into the reaction)) and an appropriate buffer and/or co-factors for optimal activity of the polymerase enzyme (e.g., $MgCl_2$ and/or KCl).

If amplification of GAS nucleic acid occurs and an amplification product is produced, the step of hybridizing results in a detectable signal based upon FRET between the members of the pair of probes. As used herein, "hybridizing" refers to the annealing of probes to an amplification product. Hybridization conditions typically include a temperature that is below the melting temperature of the probes but that avoids non-specific hybridization of the probes.

Generally, the presence of FRET indicates the presence of GAS in the biological sample, and the absence of FRET indicates the absence of GAS in the biological sample. Inadequate specimen collection, transportation delays, inappropriate transportation conditions, or use of certain collection swabs (e.g., calcium alginate or aluminum shaft) are all conditions that can affect the success and/or accuracy of the test result, however. Using the methods disclosed herein, detection of FRET within 40 cycling steps is indicative of a GAS infection.

Representative biological samples that can be used in practicing the methods of the invention include throat swabs, tissues, or bodily fluids. Biological sample collection and storage methods are known to those of skill in the art. Biological samples can be processed (e.g., by standard nucleic acid extraction methods and/or using commercial kits) to release GAS nucleic acid or, in some cases, the biological sample is contacted directly with the PCR reaction components and the appropriate oligonucleotides.

Melting curve analysis is an additional step that can be included in a cycling profile. Melting curve analysis is based on the fact that DNA melts at a characteristic temperature called the melting temperature (Tm), which is defined as the temperature at which half of the DNA duplexes have separated into single strands. The melting temperature of a DNA depends primarily upon its nucleotide composition. Thus, DNA molecules rich in G and C nucleotides have a higher Tm than those having an abundance of A and T nucleotides. By detecting the temperature at which signal is lost, the melting temperature of probes can be determined. Similarly, by detecting the temperature at which signal is generated, the annealing temperature of probes can be determined. The melting temperature(s) of the ptsI probes from the ptsI amplification product can confirm the presence of GAS in the sample.

Within each thermocycler run, control samples can be cycled as well. Positive control samples can amplify control nucleic acid template (e.g., template other than ptsI) using, for example, control primers and control probes. Positive control samples can also amplify, for example, a plasmid construct containing GAS ptsI nucleic acid molecules. Such a plasmid control can be amplified internally (e.g., within each biological sample) or in separate samples run side-by-side with the patients' samples. Each thermocycler run also should include a negative control that, for example, lacks GAS template DNA. Such controls are indicators of the success or failure of the amplification, hybridization, and/or FRET reaction. Therefore, control reactions can readily determine, for example, the ability of primers to anneal with sequence-specificity and to initiate elongation, as well as the ability of probes to hybridize with sequence-specificity and for FRET to occur.

In an embodiment, the methods of the invention include steps to avoid contamination. For example, an enzymatic method utilizing uracil-DNA glycosylase is described in U.S. Pat. Nos. 5,035,996, 5,683,896 and 5,945,313 to reduce or eliminate contamination between one thermocycler run and the next. In addition, standard laboratory containment practices and procedures are desirable when performing methods of the invention. Containment practices and procedures include, but are not limited to, separate work areas for different steps of a method, containment hoods, barrier filter pipette tips and dedicated air displacement pipettes. Consistent containment practices and procedures by personnel are desirable for accuracy in a diagnostic laboratory handling clinical samples.

Conventional PCR methods in conjunction with FRET technology can be used to practice the methods of the invention. In one embodiment, a LIGHTCYCLER™ instrument is used. A detailed description of the LIGHTCYCLER® System and real-time and on-line monitoring of PCR can be found on Roche's website. The following patent applications describe real-time PCR as used in the LIGHTCYCLER™ technology: WO 97/46707, WO 97/46714 and WO 97/46712. The LIGHTCYCLER™ instrument is a rapid thermocycler combined with a microvolume fluorometer utilizing high quality optics. This rapid thermocycling technique uses thin glass cuvettes as reaction vessels. Heating and cooling of the reaction chamber are controlled by alternating heated and ambient air. Due to the low mass of air and the high ratio of surface area to volume of the cuvettes, very rapid temperature exchange rates can be achieved within the LIGHTCYCLER™ thermal chamber. Addition of selected fluorescent dyes to the reaction components allows the PCR to be monitored in real-time and on-line. Furthermore, the cuvettes serve as an optical element for signal collection (similar to glass fiber optics), concentrating the signal at the tip of the cuvettes. The effect is efficient illumination and fluorescent monitoring of microvolume samples.

The LIGHTCYCLER™ carousel that houses the cuvettes can be removed from the instrument. Therefore, samples can be loaded outside of the instrument (in a PCR Clean Room, for example). In addition, this feature allows for the sample carousel to be easily cleaned and sterilized. The fluorometer, as part of the LIGHTCYCLER™ apparatus, houses the light source. The emitted light is filtered and focused by an epi-illumination lens onto the top of the cuvettes. Fluorescent light emitted from the sample is then focused by the same lens, passed through a dichroic mirror, filtered appropriately, and focused onto data-collecting photohybrids. The optical unit currently available in the LIGHTCYCLER™ instrument (Catalog No. 2 011 468) includes three band-pass filters (530 nm, 640 nm, and 710 nm), providing three-color detection and several fluorescence acquisition options. Data collection options include once per cycling step monitoring, fully continuous single-sample acquisition for melting curve analysis, continuous sampling (in which sampling frequency is dependent on sample number) and/or stepwise measurement of all samples after defined temperature interval.

The LIGHTCYCLER™ can be operated using a PC workstation and can utilize a Windows NT operating system. Signals from the samples are obtained as the machine positions the capillaries sequentially over the optical unit. The software can display the fluorescence signals in real-time immediately after each measurement. Fluorescent acquisition time is 10–100 msec. After each cycling step, a quantitative display of fluorescence vs. cycle number can be continually updated for all samples. The data generated can be stored for further analysis.

A common FRET technology format utilizes two hybridization probes. Each probe can be labeled with a different fluorescent moiety and the two probes are generally designed to hybridize in close proximity to each other in a target DNA molecule (e.g., an amplification product). By way of example, a donor fluorescent moiety such as fluorescein can be excited at 470 nm by the light source of the LIGHTCYCLER™ Instrument. During FRET, fluorescein transfers its energy to an acceptor fluorescent moiety such as LC™-RED 640 (LightCycler™-Red 640-N-hydroxysuccinimide ester) or LC™-RED 705 (LightCycler™-Red 705-Phosphoramidite). The acceptor fluorescent moiety then emits light of a longer wavelength (e.g., 640 nm or 705 nm, respectively), which is detected by the optical detection system of the LIGHTCYCLER™ instrument. Other donor and corresponding acceptor fluorescent moieties suitable for use in the invention are described above. Efficient FRET can only take place when the fluorescent moieties are in direct local proximity (for example, within 5 nucleotides of each other as described above) and when the emission spectrum of the donor fluorescent moiety overlaps with the absorption spectrum of the acceptor fluorescent moiety. The intensity of the emitted signal can be correlated with the number of original target DNA molecules (e.g., the number of GAS organisms).

Another FRET technology format utilizes TAQMAN® technology to detect the presence or absence of an amplification product, and hence, the presence or absence of GAS. TAQMAN® technology utilizes one single-stranded hybridization probe labeled with two fluorescent moieties. When a first fluorescent moiety is excited with light of a suitable wavelength, the absorbed energy is transferred to a second fluorescent moiety according to the principles of FRET. The second fluorescent moiety is generally a quencher molecule. During the annealing step of the PCR reaction, the labeled hybridization probe binds to the target DNA (i.e., the amplification product) and is degraded by the 5' to 3' exonuclease activity of the Taq Polymerase during the subsequent elongation phase. As a result, the excited fluorescent moiety and the quencher moiety become spatially separated from one another. As a consequence, upon excitation of the first fluorescent moiety in the absence of the quencher, the fluorescence emission from the first fluorescent moiety can be detected. By way of example, an ABI PRISM® 7700 Sequence Detection System (Applied Biosystems, Foster City, Calif.) uses TAQMAN® technology, and is suitable for performing the methods described herein for detecting GAS. Information on PCR amplification and detection using an ABI PRISM® 770 system can be found on Applied Biosystems' website.

Yet another FRET technology format utilizes molecular beacon technology to detect the presence or absence of an amplification product, and hence, the presence or absence of GAS. Molecular beacon technology uses a hybridization probe labeled with a donor fluorescent moiety and an acceptor fluorescent moiety. The acceptor fluorescent moiety is generally a quencher, and the fluorescent labels are typically located at each end of the probe. Molecular beacon technology uses a probe oligonucleotide having sequences that permit secondary structure formation (e.g., a hairpin). As a result of secondary structure formation within the probe, both fluorescent moieties are in spatial proximity when the probe is in solution. After hybridization to the target nucleic acids (i.e., the amplification products), the secondary structure of the probe is disrupted and the fluorescent moieties become separated from one another such that after excitation with light of a suitable wavelength, the emission of the first fluorescent moiety can be detected.

As an alternative to detection using FRET technology, an amplification product can be detected using a nucleic acid binding dye such as a fluorescent DNA binding dye (e.g., SYBRGREENI® or SYBRGOLD® (Molecular Probes)).

Upon interaction with the double-stranded nucleic acid, such nucleic acid binding dyes emit a fluorescence signal after excitation with light at a suitable wavelength. A nucleic acid binding dye such as a nucleic acid intercalating dye also can be used. When nucleic acid binding dyes are used, a melting curve analysis is usually performed for confirmation of the presence of the amplification product.

Articles of Manufacture

The invention further provides for articles of manufacture to detect GAS. An article of manufacture according to the present invention can include primers and probes used to detect GAS, together with suitable packaging material. Representative primers and probes provided in a kit for detection of GAS can be complementary to GAS ptsI nucleic acid molecules. Methods of designing primers and probes are disclosed herein, and representative examples of primers and probes that amplify and hybridize to GAS ptsI nucleic acid molecules are provided.

Articles of manufacture of the invention also can include one or more fluorescent moieties for labeling the probes or, alternatively, the probes supplied with the kit can be labeled. For example, an article of manufacture may include a donor fluorescent moiety for labeling one of the ptsI probes and a corresponding acceptor fluorescent moiety for labeling the other ptsI probe. Examples of suitable FRET donor fluorescent moieties and corresponding acceptor fluorescent moieties are provided herein.

Articles of manufacture of the invention also can contain a package insert having instructions thereon for using pairs of ptsI primers and ptsI probes to detect GAS in a biological sample. Articles of manufacture may additionally include reagents for carrying out the methods disclosed herein (e.g., buffers, polymerase enzymes, co-factors, or agents to prevent contamination). Such reagents may be specific for one of the commercially available instruments described herein.

The invention will be further described in the following examples, which do not limit the scope of the invention described in the claims.

EXAMPLES

Example 1

Sample Preparation

The end of a Culturette (Becton Dickinson Microbiology Systems, 4360210) was wetted with Stuart's transport medium and placed in a 0.65 ml tube of a Swab Extraction Tube System (SETS). A SETS is prepared by using a 2 ml screw capped centrifuge tubes (Sarstedt 72.693.005) and a 0.65 ml centrifuge tube (Intermountain Scientific Corporation, C-3300-2). An awl was used to puncture a hole in the bottom of the 0.65 ml centrifuge tube, which is nested inside the 2 ml tube. The handle of the swab was covered with a Bio-Screen® Biohazard wipe (Fisher 14-412-52C), broken off near the top of the tube and the lid was closed. The SETS was centrifuged at 20,800×g for 3 min in an Eppendorf 5741C. The 0.65 ml tube from the SETS was discarded. The supernatant was carefully removed and discarded with a fine-tip transfer pipet. One hundred μl water was added to the pellet, the tube was capped and placed in a 100° C. heating block for 10 min. The tube was then centrifuged at 20,800×g for 3 min. The LIGHTCYCLER™ cuvettes were placed in the LIGHTCYCLER™ rotor and 15 μl PCR mix was placed in each tube. Five μl of sample supernatant was added to the 15 μl of PCR mix in the cuvette and the cuvette was capped. The LIGHTCYCLER™ cuvette was centrifuged at 1000×g for 30 sec and placed in the LIGHTCYCLER™ apparatus.

A colony from a blood agar plate of *Streptococcus pyogenes* (ATCC 19615) was inoculated into 5 ml of Todd-Hewitt broth and incubated overnight at 37° C. for use as a positive control. The turbidity of the culture was adjusted to a McFarland 0.5 standard. A 0.5 ml sample of the culture was placed in a 2 ml screw capped tube and placed in a 100° C. heating block for 10 min. The culture was diluted 1/1000 with water and stored at 4° C. In some cases, a plasmid containing the cloned ptsI amplification product was diluted to 100 copies per μl and used as a positive control.

Example 2

Primers and Probes ptsI primers were synthesized by the Mayo Core Facility on a 0.2 nm scale, and were quantitated by UV absorption at 260 nm and mixed together to make a solution containing 25 μM of each primer.

Probes were synthesized by IT Biochem, and were dissolved in TE' to a final concentration of 20 μM (supplied with the probes and resuspended according to manufacturer's instructions). The concentration of oligonucleotides and dye was double-checked by UV absorption using the following equations (*Biochemica* 1:5–8, 1999):

$$[\text{dye}] = \frac{A_{dye}}{E_{dye}}$$

$$[\text{oligo}] = \frac{A_{260} - \left(A_{260}x\,\frac{E_{260(dye)}}{E_{dye}}\right)}{\frac{10^6}{\text{nmol}/A_{260}}}$$

To determine the natural sequence variation in the ptsI gene, the DNA sequence was determined for 11 isolates of group A streptococcus from the Mayo Foundation culture collection. The sequences obtained were aligned to the ptsI gene from the M1 strain of group A Streptococcus at the University of Oklahoma (Ferretti et al., 2001, *Proc. Natl. Acad. Sci. USA*, 98:4658–63; GenBank Accession No. AE004092). The ptsI target sequence between base pairs 170 and 1543 was found to be mostly conserved among isolates of group A streptococcus (FIG. 1). Most of the polymorphisms found were silent mutations in the third base pair of the codon. The sequence variation of the ptsI gene from a number of other streptococcus species that can be found in an oral-pharyngeal sample was determined using primers designed to conserved regions of the ptsI gene.

From these alignments, primers and probes directed toward ptsI were designed. The positions of the ptsI primers were 180 to 200 (ptsU) and 357 to 377 (ptsL) of Ferreti et al., resulting in a 198 bp PCR product. The ptsI probe positions are 242 to 260 for the fluorescein-labeled probe and 262 to 285 for the Red-640-labeled probe relative to Ferreti et al. The ptsF3 probe was provided already labeled on its 3' end with fluorescein and the ptsR1 probe was provided already labeled on its 5' end with Red-640.

The sequences of the ptsI primers are:

ptsU: 5'-AAA TGC AGT AGA AAG CTT AGG-3' (SEQ ID NO:1); and ptsL: 5'-TGC ATG TAT GGG TTA TCT TCC-3' (SEQ ID NO:2)

The sequences of the ptsI probes are:

PtsF3: 5'-TTG CTG ATC CAG AAA TGA T-3' (SEQ ID NO:3); and

PtsR1: 5'-AGC CAG GTT AAA GAA ACG ATT CGC-3' (SEQ ID NO:4).

Example 3

Conditions for Real-time PCR

Reaction mixtures for detecting GAS using ptsI primers and probes were made according to the following chart.

| Group A Strep Detection reagent | | | | |
|---|---|---|---|---|
| | Stock | 10X Stock | Volume (μl) | Final Conc. |
| Water | — | — | 45 | — |
| Mg* | 200 mM | 30 mM | 15 | 3 mM |
| Primer ptsU | 50 μM | 5 μM | 10 | 0.5 μM |
| Primer ptsL | 50 μM | 5 μM | 10 | 0.5 μM |
| Probe ptsF3 | 20 μM | 2 μM | 10 | 0.2 μM |
| Probe ptsR1 | 20 μM | 2 μM | 10 | 0.2 μM |
| Total | — | — | 100 | — |

*Final concentration of Mg in Detection reagent is 3 mM, final concentration of Mg in FastStart DNA Master Hybridization Probes Reagent is 1 mM, therefore, final concentration in PCR reaction is 4 mM.

Each 15 μl of group A Strep PCR mix contains 2 μl Group A Strep Detection reagent, 2 μl LightCycler-FastStart DNA Master Hybridization Probes Reagent (Roche 3 003 248) and 11 μl water.

Conditions for the real-time PCR using the LIGHTCYCLER™ instrument to detect GAS in biological samples were as follows. The gains were set at 1, 5, and 15 for channels F1, F2, and F3, respectively.

| Program Name/Analysis mode | Analysis mode | Cycles | Temp (° C.) | Time (sec) | Temp Transition Rate (° C./sec) | Signal Acquisition |
|---|---|---|---|---|---|---|
| Denature | None | 1 | 95 | 600 | 20 | None |
| PCR | Quantif. | 40 | 95 | 10 | 20 | None |
| | | | 55 | 10 | 20 | Single |
| | | | 72 | 8 | 20 | None |
| Melt Analysis | Melt | 1 | 95 | 0 | 20 | None |
| | | | 45 | 10 | 2 | None |
| | | | 70 | 0 | 0.2 | Continuous |
| Cool | None | 1 | 35 | 0 | 20 | None |

Example 4

Reporting Results

Analysis of the real-time PCR data is shown in FIG. 3. The melt analysis is shown in FIG. 4 and confirms the amplification product identification as group A streptococcus with melting temperatures within two degrees of the positive control, which is typically 56° C. to 58° C. Groups C and G streptococcus produce a melting peak of 50° C. to 52° C., but are not detected during the quantification portion of the real time PCR due to the presence of nucleotide polymorphisms at the probe binding sites. Thus, a reaction was reported as positive for Group A Streptococcus if a positive quantification signal with a melting curve similar to the positive control was observed. All other reactions were reported as negative.

Example 5

Validation Studies

Specificity of the method was determined by performing real-time PCR as described above on streptococcus and non-streptococcus organisms. DNA from the following organisms was tested using the ptsI primers and probes and none tested positive based on FRET detection.

| | Respiratory Panel | |
|---|---|---|
| *S. aureus* (ATCC 29213) | *S epidermidis* | human DNA |
| *E. coli* | *Ps. aeruginosa* | *K. pneumophilia* |
| *H. influenza* | Aeromonas spp | *L. jordanis* |
| *S. maltophilia* | *K. oxytoca* | *P. cepacia* |
| *P. fluorescens* | *P. mirabilis* | Acinetobacter spp |
| Morganella spp | *P. vulgaris* | *M. pneumonia* |
| *C. jejuni* | *M. catarrhalis* | *C. pneumonia* |
| *L. monocytogenes* | *L. pneumophila* | *B. bronchioseptica* |
| *B. holmesii* | *B. pertussis* | *B. parapertussis* |
| | Strep Group: | |
| *S. suis* | *S. viridans* | *L. lactis* |
| *S. anginosus* | *S. equi* | *S. uberis* |
| *S. MG-intermedius* | *S. mutans* | *E. faecium* |
| *S. bovis* | *E. faecalis* | *S. mitis* |
| *S. dysgalactiae* | *S. canis* | *S. salivarius* |
| *S. equinus* | *S. pneumococcus* | Group F Strep |
| Group B Strep non-beta | Group C strep | Group G strep |

Using plasmid-derived ptsI nucleic acid, the analytical sensitivity was determined to be less than 20 copies, of target nucleic acid per reaction.

Sensitivity was also determined by testing dilutions of a suspension of *S. pyogenes* (ATCC 19615) grown in broth overnight. The colony forming units (cfu) per ml was determined by spread plating dilutions of the culture. The sensitivity was determined to be 0.13 cfu/ml. This sensitivity is acceptable since *S. pyogenes* grows in chains of 5–15 cells, and each chain of cells is only counted as one cfu. Thus, a cfu would be expected to contain at least 5–15 copies of the target.

Example 6

Comparison of Methods

The LIGHTCYCLER™ assay for GAS using a ptsI target was compared to conventional culture (with samples cultured at the Mayo Microbiology Laboratory) and a rapid antigen test, DIRECTIGEN 1-2-3™ Group A Strep Test, from Becton Dickinson. Cultures were performed on Strep Selective Agar and positives were identified using a fluorescent antibody stain (BBL) that allows for detection of low numbers of GAS. Double swab throat swabs were used to collect patient specimens. One throat swab was used in the conventional culture and rapid antigen test procedure. The other swab was treated to extract the DNA and analyzed using the LIGHTCYCLER™ assay with the ptsI primers and probes.

The culture method is usually considered to be the "gold standard" for detecting GAS from throat swabs. The results of each assay also can be compared to all positive results. Such a method provides a standard to compare all the assays. The sensitivities of the LIGHTCYCLER™ assay using the ptsI target is more sensitive than culture and much better than the rapid antigen test for detecting GAS.

| Rapid Ag: | Culture Positive | Negative | Totals |
|---|---|---|---|
| Positive | 29 | 1 | 30 |
| Negative | 22 | 311 | 333 |
| Totals | 51 | 312 | 363 |

Prevalence (pre-test likelihood of disease) = 0.140496 = 14%
Sensitivity (true positive rate) = 0.568627 = 57%
Specificity (true negative rate) = 0.996795 = 100%

-continued

| ptsI LC: | Culture Positive | Negative | Totals |
|---|---|---|---|
| Positive | 48 | 6 | 54 |
| Negative | 3 | 306 | 309 |
| Totals | 51 | 312 | 363 |

Prevalence (pre-test likelihood of disease) = 0.140496 = 14%
Sensitivity (true positive rate) = 0.941176 = 94%
Specificity (true negative rate) = 0.980769 = 98%

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for detecting the presence or absence of Group A Streptococcus (GAS) in a biological sample from an individual, said method comprising:

performing more than one cycling step, wherein a cycling step comprises an amplifying step and a hybridizing step, wherein said amplifying step comprises contacting said sample with a pair of GAS oligonucleotide primers to produce a ptsI amplification product if a GAS ptsI nucleic acid molecule is present in said sample, wherein said hybridizing step comprises contacting said sample with a pair of GAS ptsI probes, wherein the members of said pair of ptsI probes hybridize to said amplification product within no more than five nucleotides of each other, wherein a first ptsI probe of said pair of ptsI probes is labeled with a donor fluorescent, moiety and wherein a second ptsI probe of said pair of ptsI probes is labeled with a corresponding acceptor fluorescent moiety; and detecting the presence or absence of fluorescence resonance energy transfer (FRET) between said donor fluorescent moiety of said first ptsI probe and said acceptor fluorescent moiety of said second ptsI probe, wherein the presence of FRET is indicative of the presence of GAS in said biological sample, and wherein the absence of FRET is indicative of the absence of GAS in said biological sample.

2. The method of claim 1, wherein said pair of oligonucleotide primers comprises a first ptsI primer and a second ptsI primer, wherein said first ptsI primer comprises the sequence 5'-AAA TGC AGT AGA AAG CTT AGG-3' (SEQ ID NO:1), and wherein said second ptsI primer comprises the sequence

5'-TGC ATG TAT GGG TTA TCT TCC-3' (SEQ ID NO:2).

3. The method of claim 1, wherein said first ptsI probes comprises the sequence

5'-TTG CTG ATC CAG AAA TGA T-3' (SEQ ID NO:3), and wherein said second ptsI probe comprises the sequence

5'-AGC CAG GTT AAA GAA ACG ATT CGC-3' (SEQ ID NO:4).

4. The method of claim 1, wherein the members of said pair of ptsI probes hybridize within no more than two nucleotides of each other.

5. The method of claim 1, wherein the members of said pair of ptsI probes hybridize within no more than one nucleotide of each other.

6. The method of claim 1, wherein said donor fluorescent moiety is fluorescein.

7. The method of claim 1, wherein said detecting step comprises exciting said biological sample at a wavelength absorbed by said donor fluorescent moiety and visualizing and/or measuring the wavelength emitted by said acceptor fluorescent moiety.

8. The method of claim 1, wherein said detecting comprises quantitating said FRET.

9. The method of claim 1, wherein said detecting step is performed after each cycling step.

10. The method of claim 1, wherein said detecting step is performed in real-time.

11. The method of claim 1, further comprising determining the melting temperature between one or both of said ptsI probe and said ptsI amplification product, wherein said melting temperature confirms said presence or said absence of said GAS.

12. The method of claim 1, wherein the presence of said FRET within 50 cycles is indicative of the presence of a GAS infection in said individual.

13. The method of claim 1, wherein the presence of said FRET within 40 cycles is indicative of the presence of a GAS infection in said individual.

14. The method of claim 1, wherein the presence of said FRET within 30 cycles is indicative of the presence of a GAS infection in said individual.

15. The method of claim 1, further comprising preventing amplification of a contaminant nucleic acid.

16. The method of claim 15, wherein said preventing comprises performing said amplification step in the presence of uracil.

17. The method of claim 16, wherein said preventing further comprises treating said biological sample with uracil-DNA glycosylase prior to a first amplification step.

18. The method of claim 1, wherein said biological sample is selected from the group consisting of throat swabs, tissues and bodily fluids.

19. The method of claim 1, wherein said cycling step is performed on a control sample.

20. The method of claim 19, wherein said control sample comprises said GAS ptsI nucleic acid molecule.

21. The method of claim 1, wherein said cycling step further comprises using a pair of control primers and a pair of control probes, wherein said control primers and said control probes are other than said oligonucleotide primers and said ptsI probes, respectively, wherein a control amplification product is produced if control template is present in said sample, wherein said control probes hybridize to said control amplification product.

22. An article of manufacture, comprising:

a pair of GAS oligonucleotide primers;

a pair of GAS ptsI probes; and a donor fluorescent moiety and a corresponding acceptor fluorescent moiety.

23. The article of manufacture of claim 22, wherein said pair of oligonucleotide primers comprises a first ptsI primer and a second ptsI primer, wherein said first ptsI primer comprises the sequence 5'-AAA TGC AGT AGA AAG CTT AGG-3' (SEQ ID NO: 1), and wherein said second ptsI primer comprises the sequence

5'-TGC ATG TAT GGG TTA TCT TCC-3' (SEQ ID NO:2).

24. The article of manufacture of claim 22, wherein said pair of ptsI probes comprises a first ptsI probe and a second ptsI probe, wherein said first ptsI probe comprises the sequence 5'-TTG CTG ATC CAG AAA TGA T-3' (SEQ ID NO:3), and wherein said second ptsI probe comprises the sequence

5'-AGC CAG GTT AAA GAA ACG ATT CGC-3' (SEQ ID NO:4).

25. The article of manufacture of claim 22, wherein said pair of ptsI probes comprises a first ptsI probe labeled with said donor fluorescent moiety and a second ptsI probe labeled with said corresponding acceptor fluorescent moiety.

26. The article of manufacture of claim 22, further comprising a package label or package insert having instructions thereon for using said pair of oligonucleotide primers and said pair of ptsI probes to detect the presence or absence of GAS in a biological sample.

27. A method for detecting the presence or absence of GAS in a biological sample from an individual, said method comprising:

performing more than one cycling step, wherein a cycling step comprises an amplifying step and a hybridizing step, wherein said amplifying step comprises contacting said sample with a pair of GAS oligonucleotide primers to produce a ptsI amplification product if a GAS ptsI nucleic acid molecule is present in said sample, wherein said hybridizing step comprises contacting said sample with a GAS ptsI probe, wherein said ptsI probe is labeled with a donor fluorescent moiety and a corresponding acceptor fluorescent moiety; and detecting the presence or absence of fluorescence resonance energy transfer (FRET) between said donor fluorescent moiety and said acceptor fluorescent moiety of said ptsI probe, wherein the presence or absence of FRET is indicative of the presence or absence of GAS in said sample.

28. The method of claim 27, wherein said amplification employs a polymerase enzyme having 5' to 3' exonuclease activity.

29. The method of claim 28, wherein said donor and acceptor fluorescent moieties are within no more than 5 nucleotides of each other on said probe.

30. The method of claim 29, wherein said acceptor fluorescent moiety is a quencher.

31. The method of claim 27, wherein said ptsI probe comprises a nucleic acid sequence that permits secondary structure formation, wherein said secondary structure formation results in spatial proximity between said donor and said acceptor fluorescent moiety.

32. The method of claim 31, wherein said acceptor fluorescent moiety is a quencher.

33. A method for detecting the presence or absence of GAS in a biological sample from an individual, said method comprising:

performing more than one cycling step, wherein a cycling step comprises an amplifying step and a dye-binding step, wherein said amplifying step comprises contacting said sample with a pair of GAS oligonucleotide primers to produce a ptsI amplification product if a GAS ptsI nucleic acid molecule is present in said sample, wherein said dye-binding step comprises contacting said ptsI amplification product with a nucleic acid binding dye; and detecting the presence or absence of binding of said nucleic acid binding dye to said amplification product, wherein the presence of binding is indicative of the presence of GAS in said sample, and wherein the absence of binding is indicative of the absence of GAS in said sample.

34. The method of claim 33, wherein said nucleic acid binding dye is ethidium bromide.

35. The method of claim 34, further comprising determining the melting temperature between said ptsI amplification product and said nucleic acid binding dye, wherein said melting temperature confirms said presence or absence of said GAS.

* * * * *

UNITED STATES PATENT AND TRADEMARK OFFICE

CERTIFICATE OF CORRECTION

PATENT NO. : 6,593,093 B1
DATED : July 15, 2003
INVENTOR(S) : James R. Uhl and Franklin R. Cockerill III It is certified that error appears in the above-identified patent and that said Letters Patent is hereby corrected as shown below:

Title page,
Item [56], References Cited, "Luesink et al." reference, please delete "ptsHI" and insert -- ptsH1 -- therefore; and please delete "18(3)P764-771" and insert -- 181:764-771 -- therefore;
"Steed et al" reference, plesae delete "*Streptococuss pyrgenes*" and insert -- *Streptococcus pyrogenes* -- therefore;

Column 42,
Line 59, please delete the comma afte "fluorescent";

Column 43,
Line 12, please delete "probes" and insert -- probe -- therefore;
Line 31, please insert -- step -- after "detecting".

Signed and Sealed this

Thirty-first Day of August, 2004

JON W. DUDAS
*Director of the United States Patent and Trademark Office*

SEQUENCE LISTING

```
<160> NUMBER OF SEQ ID NOS: 17

<210> SEQ ID NO 1
<211> LENGTH: 21
<212> TYPE: DNA
<213> ORGANISM: Artificial Sequence
<220> FEATURE:
<223> OTHER INFORMATION: Oligonucleotide

<400> SEQUENCE: 1

aaatgcagta gaaagcttag g                                            21


<210> SEQ ID NO 2
<211> LENGTH: 21
<212> TYPE: DNA
<213> ORGANISM: Artificial Sequence
<220> FEATURE:
<223> OTHER INFORMATION: Oligonucleotide

<400> SEQUENCE: 2

tgcatgtatg ggttatcttc c                                            21


<210> SEQ ID NO 3
<211> LENGTH: 19
<212> TYPE: DNA
<213> ORGANISM: Artificial Sequence
<220> FEATURE:
<223> OTHER INFORMATION: Oligonucleotide

<400> SEQUENCE: 3

ttgctgatcc agaaatgat                                               19


<210> SEQ ID NO 4
<211> LENGTH: 24
<212> TYPE: DNA
<213> ORGANISM: Artificial Sequence
```

-continued

<220> FEATURE:
<223> OTHER INFORMATION: Oligonucleotide

<400> SEQUENCE: 4
agccaggtta aagaaacgat tcgc 24

<210> SEQ ID NO 5
<211> LENGTH: 1803
<212> TYPE: DNA
<213> ORGANISM: Group A Streptococcus
<220> FEATURE:
<223> OTHER INFORMATION: ptsI sequence from Oklahoma University M1 strain
<300> PUBLICATION INFORMATION:
<301> AUTHORS: Ferretti et al.
<303> JOURNAL: Proc. Natl. Acad. Sci. USA
<304> VOLUME: 98
<306> PAGES: 4658-4663
<307> DATE: 2001-01-01

<400> SEQUENCE: 5
atgacagaaa tgcttaaagg aattgcagcc tcagacggcg ttgctgttgc taaagcatat 60
ctactagttc agccggattt gtcatttgag actgttacag tcgcagatac aaatgcagaa 120
gaagctcgcc ttgatgttgc actccaagct gcacaagacg agctttctgt tatccgtgaa 180
aatgcagtag aaagcttagg tgaagaagca gcagccgttt ttgatgccca tttgatggtt 240
cttgctgatc cagaaatgat cagccaggtt aaagaaacga ttcgcgcaaa acaaacgaat 300
gcagaaacag gtcttaaaga agtgactgac atgttcatca ccatctttga aggcatggaa 360
gataacccat acatgcaaga acgtgcagcg gacatccgcg acgttgcaaa acgtgtgttg 420
gctcaccttt taggtgtaaa acttccaaat ccagctacaa tcaatgaaga atcaatcgtt 480
atcgcacacg atttgacacc ttcagatact gctcaactta acaaacaatt tgtaaaagca 540
tttgttacaa atatcggtgg tcgtacaagt cactcagcta tcatggcacg tacacttgag 600
atcgctgcgg tacttggaac aaatgatatt acaaaacgtg ttaaagatgg tgatgtgatt 660
gccgttaatg gtatcactgg tgaagtgatt atcgatccaa gcgaagatca agtacttgct 720
tttaaagaag ctggtgcggc ttatgccaaa caaaaagcag agtggtctct ccttaaagat 780
gcgcacactg aaacagctga tggcaaacac tttgaattgg ctgctaatat cggtacgcct 840
aaagacgttg aaggtgttaa tgacacagct gatggcaaac actttgaatt ggctgctaat 900
atcggtacgc ctaaagacgt tgaaggtgtt aatgacaatg gtgctgaagc tgttggcctt 960
taccgtactg agttcttgta catggattct caagacttcc caactgaaga cgaacaatac 1020
gaagcttaca aggcagtgct tgaaggcatg aatggcaaac ctgttgtggt tcgtacgatg 1080
gatattggtg gcgacaagga acttccttac tttgaccttc caaaagaaat gaatccattc 1140
cttggtttcc gtgctcttcg tatttccatc tctgaaactg gggatgccat gttccgcaca 1200
caaatgcgtg cgcttcttcg tgcctctgtt cacggacaac ttcgtattat gttcccaatg 1260
gttgcgcttc ttaaagaatt ccgtgctgca aaagcaatct ttgacgaaga aaaagcaaac 1320
ttgcttgcag aaggcgttgc ggttgctgat gacatccaag ttggtatcat gattgagatt 1380
cctgcagctg ctatgcttgc agaccaattt gctaaggaag ttgatttctt ctcaattgga 1440
acaaacgacc ttatccaata cactatggca gcagaccgta tgaacgaaca agtatcatac 1500
ctttaccaac catacaaccc atcaatatta cgtttgatca acaatgtgat caaagcagcg 1560
cacgctgaag gtaaatgggc aggtatgtgt ggtgagatgg caggtgacca acaagctgtt 1620
ccacttcttg tcggaatggg cttggatgag ttttctatgt cagcaacttc agtacttcgt 1680

-continued acgcgtagtt taatgaagaa acttgactct gctaagatgg aagaatatgc aaatcgtgcg 1740
cttacagaat gttcaacagc agaagaagtt cttgaacttt ctaaagaata cgtttctgaa 1800
gat 1803

<210> SEQ ID NO 6
<211> LENGTH: 629
<212> TYPE: PRT
<213> ORGANISM: Group A Streptococcus
<220> FEATURE:
<223> OTHER INFORMATION: ptsI sequence from Oklahoma University M1 strain
<300> PUBLICATION INFORMATION:
<301> AUTHORS: Ferretti et al.
<303> JOURNAL: Proc. Natl. Acad. Sci. USA
<304> VOLUME: 98
<306> PAGES: 4658-4663
<307> DATE: 2001-01-01

<400> SEQUENCE: 6

```
Met Glu Thr Thr Glu Met Glu Thr Leu Lys Gly Ile Ala Ala Ser Asp
 1               5                  10                  15

Gly Val Ala Val Ala Lys Ala Tyr Leu Leu Val Gln Pro Asp Leu Ser
            20                  25                  30

Phe Glu Thr Val Thr Val Ala Asp Thr Asn Ala Glu Glu Ala Arg Leu
        35                  40                  45

Asp Val Ala Leu Gln Ala Ala Gln Asp Glu Leu Ser Val Ile Arg Glu
    50                  55                  60

Asn Ala Val Glu Ser Leu Gly Glu Glu Ala Ala Ala Val Phe Asp Ala
65                  70                  75                  80

His Leu Met Glu Thr Val Leu Ala Asp Pro Glu Met Glu Thr Ile Ser
                85                  90                  95

Gln Val Lys Glu Thr Ile Arg Ala Lys Gln Thr Asn Ala Glu Thr Gly
            100                 105                 110

Leu Lys Glu Val Thr Asp Met Glu Thr Phe Ile Thr Ile Phe Glu Gly
        115                 120                 125

Met Glu Thr Glu Asp Asn Pro Tyr Met Glu Thr Gln Glu Arg Ala Ala
    130                 135                 140

Asp Ile Arg Asp Val Ala Lys Arg Val Leu Ala His Leu Leu Gly Val
145                 150                 155                 160

Lys Leu Pro Asn Pro Ala Thr Ile Asn Glu Glu Ser Ile Val Ile Ala
                165                 170                 175

His Asp Leu Thr Pro Ser Asp Thr Ala Gln Leu Asn Lys Gln Phe Val
            180                 185                 190

Lys Ala Phe Val Thr Asn Ile Gly Gly Arg Thr Ser His Ser Ala Ile
        195                 200                 205

Met Glu Thr Ala Arg Thr Leu Glu Ile Ala Ala Val Leu Gly Thr Asn
    210                 215                 220

Asp Ile Thr Lys Arg Val Lys Asp Gly Asp Val Ile Ala Val Asn Gly
225                 230                 235                 240

Ile Thr Gly Glu Val Ile Ile Asp Pro Ser Glu Asp Gln Val Leu Ala
                245                 250                 255

Phe Lys Glu Ala Gly Ala Ala Tyr Ala Lys Gln Lys Ala Glu Trp Ser
            260                 265                 270

Leu Leu Lys Asp Ala His Thr Glu Thr Ala Asp Gly Lys His Phe Glu
        275                 280                 285

Leu Ala Ala Asn Ile Gly Thr Pro Lys Asp Val Glu Gly Val Asn Asp
```

-continued

```
    290                 295                 300

Asn Gly Ala Glu Ala Val Gly Leu Tyr Arg Thr Glu Phe Leu Tyr Met
305                 310                 315                 320

Glu Thr Asp Ser Gln Asp Phe Pro Thr Glu Asp Glu Gln Tyr Glu Ala
                325                 330                 335

Tyr Lys Ala Val Leu Glu Gly Met Glu Thr Asn Gly Lys Pro Val Val
            340                 345                 350

Val Arg Thr Met Glu Thr Asp Ile Gly Gly Asp Lys Glu Leu Pro Tyr
        355                 360                 365

Phe Asp Leu Pro Lys Glu Met Glu Thr Asn Pro Phe Leu Gly Phe Arg
    370                 375                 380

Ala Leu Arg Ile Ser Ile Ser Glu Thr Gly Asp Ala Met Glu Thr Phe
385                 390                 395                 400

Arg Thr Gln Met Glu Thr Arg Ala Leu Leu Arg Ala Ser Val His Gly
                405                 410                 415

Gln Leu Arg Ile Met Glu Thr Phe Pro Met Glu Thr Val Ala Leu Leu
            420                 425                 430

Lys Glu Phe Arg Ala Ala Lys Ala Val Phe Asp Glu Glu Lys Ala Asn
        435                 440                 445

Leu Leu Ala Glu Gly Val Ala Val Ala Asp Asp Ile Gln Val Gly Ile
    450                 455                 460

Met Glu Thr Ile Glu Ile Pro Ala Ala Ala Met Glu Thr Leu Ala Asp
465                 470                 475                 480

Gln Phe Ala Lys Glu Val Asp Phe Phe Ser Ile Gly Thr Asn Asp Leu
                485                 490                 495

Ile Gln Tyr Thr Met Glu Thr Ala Ala Asp Arg Met Glu Thr Asn Glu
            500                 505                 510

Gln Val Ser Tyr Leu Tyr Gln Pro Tyr Asn Pro Ser Ile Leu Arg Leu
        515                 520                 525

Ile Asn Asn Val Ile Lys Ala Ala His Ala Glu Gly Lys Trp Ala Gly
    530                 535                 540

Met Glu Thr Cys Gly Glu Met Glu Thr Ala Gly Asp Gln Gln Ala Val
545                 550                 555                 560

Pro Leu Leu Val Gly Met Glu Thr Gly Leu Asp Glu Phe Ser Met Glu
                565                 570                 575

Thr Ser Ala Thr Ser Val Leu Arg Thr Arg Ser Leu Met Glu Thr Lys
            580                 585                 590

Lys Leu Asp Ser Ala Lys Met Glu Thr Glu Glu Tyr Ala Asn Arg Ala
        595                 600                 605

Leu Thr Glu Cys Ser Thr Ala Glu Glu Val Leu Glu Leu Ser Lys Glu
    610                 615                 620

Tyr Val Ser Glu Asp
625
```

<210> SEQ ID NO 7
<211> LENGTH: 1379
<212> TYPE: DNA
<213> ORGANISM: Group A Streptcoccus
<220> FEATURE:
<223> OTHER INFORMATION: ptsI sequence from isolate no. 6

<400> SEQUENCE: 7

```
gttatccgtg aaaatgcagt agaaagctta ggtgaagaag cagcagccgt ttttgatgcc     60

catttgatgg ttcttgctga tccagaaatg atcagccagg ttaaagaaac gattcgcgca    120
```

-continued

```
aaacaaacga atgcagaaac aggtcttaaa gaagtgactg acatgttcat caccatcttt    180

gaaggcatgg aagataaccc atacatgcaa gaacgtgcag cggacatccg cgacgttgca    240

aaacgtgtgt tggctcacct tttaggtgta aaacttccaa atccagctac aatcaatgaa    300

gaatcaatcg ttatcgcaca cgatttgaca ccttcagata ctgctcaact taacaaacaa    360

tttgtaaaag catttgttac aaatatcggt ggtcgtacaa gtcactcagc tatcatggca    420

cgtacacttg agatcgctgc ggtacttgga acaaatgata ttacaaaacg tgttaaagat    480

ggtgatgtga ttgccgttaa tggtatcact ggtgaagtga ttatcgatcc aagcgaagat    540

caagtacttg ctgcagagtg gtctctcctt aaagatgcgc acactgaatt taaagaagct    600

ggtgcggctt atgccaaaca aaaaacagct gatggcaaac actttgaatt ggctgctaat    660

atcggtacgc ctaaagacgt tgaaggtgtt aatgacaatg gtgctgaagc tgttggcctt    720

taccgtactg agttcttgta catggattct caagacttcc caactgaaga cgaacaatac    780

gaagcttaca aggcagtgct tgaaggcatg aatggcaaac ctgttgtggt tcgtacgatg    840

gatattggtg gcgacaagga acttccttac tttgaccttc caaaagaaat gaatccattc    900

cttggtttcc gtgctcttcg tatttccatc tctgaaactg gggatgccat gttccgcaca    960

caaatgcgtg cgcttcttcg tgcctctgtt cacggacaac ttcgtattat gttcccaatg   1020

gttgcgcttc ttaaagaatt ccgtgctgca aaagcaatct ttgacgaaga aaaagcaaac   1080

ttgcttgcag aaggcgttgc ggttgctgat gacatccaag ttggtatcat gattgagatt   1140

cctgcagctg ctatgcttgc agaccaattt gctaaggaag ttgatttctt ctcaattgga   1200

acaaacgacc ttatccaata cactatggca gcagaccgta tgaacgaaca agtatcatac   1260

ctttaccaac catacaaccc atcaatatta cgtttgatca acaatgtgat caaagcagcg   1320

cacgctgaag gtaaatgggc aggtatgtgt ggtgagatgg caggtgacca acaagctgt    1379
```

```
<210> SEQ ID NO 8
<211> LENGTH: 1384
<212> TYPE: DNA
<213> ORGANISM: Group A Streptococcus
<220> FEATURE:
<223> OTHER INFORMATION: ptsI sequence from isolate no. 5

<400> SEQUENCE: 8

tgttatccgt gaaaatgcag tagaaagctt aggtgaagaa gcagcagccg tttttgatgc     60

ccatttgatg gttcttgctg atccagaaat gatcagccag gttaaagaaa cgattcgcgc    120

aaaaacaaacg aatgcagaaa caggtcttaa agaagtgact gacatgttca tcaccatctt    180

tgaaggcatg gaagataacc catacatgca agaacgtgca gcggacatcc gcgacgttgc    240

aaaacgtgtg ttggctcacc ttttaggtgt aaaacttcca aatccagcta caatcaatga    300

agaatcaatc gttatcgcac acgatttgac accttcagat actgctcaac ttaacaaaca    360

atttgtaaaa gcatttgtta caaatatcgg tggtcgtaca agtcactcag ctatcatggc    420

acgtacactt gagatcgctg cggtacttgg aacaaatgat attacaaaac gtgttaaaga    480

tggtgatgtg attgccgtta atggtatcac tggtgaagtg attatcgatc caagcgaaga    540

tcaagtactt gcttttaaag aagctggtgc ggcttatgcc aaacaaaaag cagagtggtc    600

tctccttaaa gatgcgcaca ctgaaacagc tgatggcaaa cactttgaat tggctgctaa    660

tatcggtacg cctaaagacg ttgaaggtgt taatgacaat ggcgctgaag ctgttggcct    720

ttaccgtact gagttcttgt acatggattc tcaagacttc ccaactgaag acgaacaata    780

cgaagcttac aaagcagtgc ttgaaggcat gaatggcaaa cctgttgtgg ttcgtacaat    840
```

-continued

```
ggatattggt ggagataagg aacttcctta ctttgacctt ccaaaagaaa tgaatccatt    900
ccttggtttc cgtgctcttc gtatttccat ctctgaaact ggggatgcca tgttccgcac    960
acaaatgcgt gcgcttcttc gcgcctctgt tcacggacaa cttcgtatca tgttcccaat   1020
ggtagcactt cttaaagaat tccgtgctgc aaaagcaatc tttgatgaag aaaaagcaaa   1080
cttgcttgca gaaggcgttg cggttgctga tgacatccaa gttggtatca tgattgagat   1140
tcctgcagct gctatgcttg cagaccaatt tgctaaggaa gttgatttct tctcaattgg   1200
aacaaacgac cttatccaat acactatggc agcagaccgt atgaacgaac aagtatcata   1260
cctttaccaa ccatacaacc catcaatatt acgtttgatc aacaatgtga tcaaagcagc   1320
gcacgctgaa ggtaaatggg caggtatgtg tggtgagatg gcaggtgacc aacaagctgt   1380
tcca                                                                1384
```

<210> SEQ ID NO 9
<211> LENGTH: 1385
<212> TYPE: DNA
<213> ORGANISM: Group A Streptococcus
<220> FEATURE:
<223> OTHER INFORMATION: ptsI sequence from isolate no. 7

<400> SEQUENCE: 9

```
tgttatccgt gaaaatgcag tagaaagctt aggtgaagaa gcagcagccg tttttgatgc     60
ccatttgatg gttcttgctg atccagaaat gatcagccag gttaaagaaa cgattcgcgc    120
aaaacaaacg aatgcagaaa caggtcttaa agaagtgact gacatgttca tcaccatctt    180
tgaaggcatg gaagataacc catacatgca agaacgtgca gcggacatcc gcgacgttgc    240
aaaacgtgtg ttggctcacc ttttaggtgt aaaacttcca aatccagcta caatcaatga    300
agaatcaatc gttatcgcac acgatttgac accttcagat actgctcaac ttaacaaaca    360
atttgtaaaa gcatttgtta caaatatcgg tggtcgtaca agtcactcag ctatcatggc    420
acgtacactt gagatcgctg cggtacttgg aacaaatgat attacaaaac gtgttaaaga    480
tggtgatgtg attgccgtta atggtatcac tggtgaagtg attatcgatc caagcgaaga    540
tcaagtactt gcttttaaag aagctggtgc ggcttatgcc aaacaaaaag cagagtggtc    600
tctccttaaa gatgcgcaca ctgaaacagc tgatggcaaa cactttgaat tggctgctaa    660
tatcggtacg cctaaagacg ttgaaggtgt taatgacaat ggtgctgaag ctgttggcct    720
ttaccgtact gagttcttgt acatggattc tcaagacttc ccaactgaag acgaacaata    780
cgaagcttac aaggcagtgc ttgaaggcat gaatggcaaa cctgttgtgg ttcgtacgat    840
ggatattggt ggcgacaagg aacttcctta ctttgacctt ccaaaagaaa tgaatccatt    900
ccttggtttc cgtgctcttc gtatttccat ctctgaaact ggggacgcca tgttccgcac    960
acaaatacgt gcgcttcttc gcgcctctgt tcacggacaa cttcgtatta tgttcccaat   1020
ggttgcgctt cttaaagaat tccgtgctgc aaaagcagtc tttgatgaag aaaaagcaaa   1080
cttgcttgca gaaggcgttg cggttgctga tgacatccaa gttggtatca tgattgagat   1140
tcctgcagct gctatgcttg cagaccaatt tgctaaggaa gttgatttct tctcaattgg   1200
aacaaacgac cttatccaat acactatggc agcagaccgt atgaacgaac aagtatcata   1260
cctttaccaa ccatacaacc catcaatatt acgtttgatc aacaatgtga tcaaagcagc   1320
gcacgctgaa ggtaaatggg caggtatgtg tggtgagatg gcaggtgacc aacaagctgt   1380
tccac                                                               1385
```

-continued

<210> SEQ ID NO 10
<211> LENGTH: 1384
<212> TYPE: DNA
<213> ORGANISM: Group A Streptococcus
<220> FEATURE:
<223> OTHER INFORMATION: ptsI sequence from isolate no. 8

<400> SEQUENCE: 10

```
gttatccgtg aaaatgcagt agaaagctta ggtgaagaag cagcagccgt tttgatgcc     60
catttgatgg ttcttgctga tccagaaatg atcagccagg ttaaagaaac gattcgcgca    120
aaacaaacga atgcagaaac aggtcttaaa gaagtgactg acatgttcat caccatcttt    180
gaaggcatgg aagataaccc atacatgcaa gaacgtgcag cggacatccg cgacgttgca    240
aaacgtgtgt tggctcacct tttaggtgta aaacttccaa atccagctac aatcaatgaa    300
gaatcaatcg ttatcgcaca cgatttgaca ccttcagata ctgctcaact taacaaacaa    360
tttgtaaaag catttgttac aaatatcggt ggtcgtacaa gtcactcagc tatcatggca    420
cgtacacttg agatcgctgc ggtacttgga acaaatgata ttacaaaacg tgttaaagat    480
ggtgatgtga ttgccgttaa tggtatcact ggtgaagtga ttatcgatcc aagcgaagat    540
caagtacttg cttttaaaga agctggtgcg gcttatgcca aacaaaaagc agagtggtct    600
ctccttaaag atgcgcatac tgaaacagct gatggcaaac actttgaatt ggctgctaat    660
atcggtacac ctaaagacgt tgaaggtgtt aatgacaatg gcgctgaagc tgttggcctt    720
taccgtactg agttcttgta catggattct caagacttcc caactgaaga cgaacaatac    780
gaagcttaca aggcagtgct tgaaggcatg aatggcaaac ctgttgtggt tcgtacgatg    840
gatattggtg gcgacaagga acttccttac tttgaccttc caaaagaaat gaatccattc    900
cttggtttcc gtgctcttcg tatttccatc tctgaaactg ggatgccat gttccgcaca     960
caaatgcgtg cgcttcttcg tgcctctgtt cacggacaac ttcgtattat gttcccaatg   1020
gttgcccttc ttaaagaatt ccgtgctgca aaagcagtct ttgatgaaga aaaagcaaac   1080
ttgcttgcag aaggcgttgc ggttgctgat gacatccaag ttggtatcat gattgagatt   1140
cctgcagctg ctatgcttgc agaccaattt gctaaggaag ttgatttctt ctcaattgga   1200
acaaacgacc ttatccaata cactatggca gcagaccgta tgaacgaaca agtatcatac   1260
ctttaccaac catacaaccc atcaatatta cgtttgatca acaatgtgat caaagcagcg   1320
cacgctgaag gtaaatgggc aggtatgtgt ggtgagatgg caggtgacca acaagctgtt   1380
ccac                                                                1384
```

<210> SEQ ID NO 11
<211> LENGTH: 1390
<212> TYPE: DNA
<213> ORGANISM: Group A Streptococcus
<220> FEATURE:
<223> OTHER INFORMATION: ptsI sequence from isolate no. 9

<400> SEQUENCE: 11

```
caagacgagc tttctgttat ccgtgaaaat gcagtagaaa gcttaggtga agaagcagca     60
gccgtttttg atgcccattt gatggttctt gctgatccag aaatgatcag ccaggttaaa    120
gaaacgattc gcgcaaaaca aacgaatgca gaaacaggtc ttaaagaagt gactgacatg    180
ttcatcacca tctttgaagg catggaagat aacccataca tgcaagaacg cgcagcggac    240
atccgcgacg ttgcaaaacg tgtgttggct caccttttag gtgtaaaact tccaaatcca    300
gctacaatca atgaagaatc aatcgttatc gcacacgatt tgacaccttc agatactgct    360
```

-continued

```
caacttaaca aacaatttgt aaaagcattt gttacaaata tcggtggtcg tacaagtcac    420

tcagctatca tggcacgtac acttgagatc gctgcggtac ttggaacaaa tgatattaca    480

aaacgtgtta aagatggtga tgtgattgcc gttaatggta tcactggtga agtgattatc    540

gatccaagcg aagatcaagt acttgctttt aaagaagctg gtgcggctta tgccaaacaa    600

aaagcagagt ggtctctcct taaagatgcg catactgaaa cagctgatgg caaacacttt    660

gaattggctg ctaatatcgg tacacctaaa gacgttgaag gtgttaatga caatggcgct    720

gaagctgttg gcctttaccg tactgagttc ttgtacatgg attctcaaga cttcccaact    780

gaagacgaac aatacgaagc ttacaaggca gtgcttgaag gcatgaatgg caaacctgtt    840

gtggttcgta cgatggatat tggtggcgac aaggaacttc cttactttga ccttccaaaa    900

gaaatgaatc cattccttgg tttccgtgct cttcgtattt ccatctctga aactggggat    960

gccatgttcc gcacacaaat gcgtgcgctt cttcgtgcct ctgttcacgg acaacttcgt   1020

attatgttcc caatggttgc ccttcttaaa gaattccgtg ctgcaaaagc agtctttgat   1080

gaagaaaaag caaacttgct tgcagaaggc gttgcggttg ctgatgacat ccaagttggt   1140

atcatgattg agattcctgc agctgctatg cttgcagacc aatttgctaa ggaagttgat   1200

ttcttctcaa ttggaacaaa cgaccttatc caatacacta tggcagcaga ccgtatgaac   1260

gaacaagtat catacccttta ccaaccatac aacccatcaa tattacgttt gatcaacaat   1320

gtgatcaaag cagcgcacgc tgaaggtaaa tgggcaggta tgtgtggtga gatggcaggt   1380

gaccaacaag                                                          1390
```

```
<210> SEQ ID NO 12
<211> LENGTH: 1323
<212> TYPE: DNA
<213> ORGANISM: Group A Streptococcus
<220> FEATURE:
<223> OTHER INFORMATION: ptsI sequence from isolate no. 2

<400> SEQUENCE: 12

cagtagaaag cttaggtgaa gaagcagcag ccgtttttga tgcccatttg atggttcttg     60

ctgatccaga aatgattagc caggttaaag aaacgattcg cgcaaaacaa acgaatgcag    120

aaacaggtct taaagaagtg actgacatgt tcatcaccat ctttgaaggc atggaagata    180

acccatacat gcaagaacgt gcagcggaca ttcgcgacgt tgcaaaacgt gtgttggctc    240

acctttagg tgtaaaactt ccaaatccag ctacaatcaa tgaagaatca atcgttatcg    300

cacacgattt gacaccttca gatactgctc aacttaacaa acaatttgta aaagcatttg    360

ttacaaatat cggtggtcgt acaagtcact cagctatcat ggcacgtaca cttgagatcg    420

ctgcggtact tggaacaaat gatattacaa aacgtgttaa agatggtgat gtgattgccg    480

ttaatggtat cactggtgaa gtgattatcg atccaagcga agatcaagta cttgctttta    540

aagaagctgg tgcggcttat gccaaacaaa aagcagagtg gtctctcctt aaagatgcgc    600

atactgaaac agctgatggc aaacactttg aattggctgc taatatcggt acgcctaaag    660

acgttgaagg tgttaatgac aatggcgctg aagctgttgg cctttaccgt actgagttct    720

tgtacatgga ttctcaagac ttcccaactg aagacgaaca atacgaagct tacaaggcag    780

tgcttgaagg catgaatggc aaacctgtcg tggttcgtac gatggatatt ggtggcgaca    840

aggaacttcc ttactttgac cttccaaaag aaatgaatcc attccttggt ttccgtgctc    900

ttcgtatttc catctctgaa actggggatg ccatgttccg cacacaaatg cgtgcgcttc    960
```

-continued

```
ttcgtgcctc tgttcacgga caacttcgta ttatgttccc aatggttgcg cttcttaaag   1020

aattccgtgc tgcaaaagca ggcgttgcgg ttgctgatga cattcaagtt ggtatcatga   1080

ttgagattcc tgcagctgct atgcttgcag accaatttgc taaggaagtt gatttcttct   1140

caattggaac aaacgacctt atccaataca ctatggcagc agaccgtatg aacgaacaag   1200

tatcatacct ttaccaacca tacaacccat caatattacg tttgatcaac aatgtgatca   1260

aagcagcgca cgctgaaggt aaatgggcag gtatgtgtgg tgagatggca ggtgaccaac   1320

aag                                                                 1323
```

<210> SEQ ID NO 13
<211> LENGTH: 1379
<212> TYPE: DNA
<213> ORGANISM: Group A Streptococcus
<220> FEATURE:
<223> OTHER INFORMATION: ptsI sequence from isolate no. 4

<400> SEQUENCE: 13

```
gttatccgtg aaaatgcagt agaaagctta ggtgaagaag cagcagccgt ttttgatgcc     60

catttgatgg ttcttgctga tccagaaatg attagccagg ttaaagaaac gattcgcgca    120

aaacaaacga atgcagaaac aggtcttaaa gaagtgactg acatgttcat caccatcttt    180

gaaggcatgg aagataaccc atacatgcaa gaacgtgcag cggacattcg cgacgttgca    240

aaacgtgtgt tggctcacct tttaggtgta aaacttccaa atccagctac aatcaatgaa    300

gaatccatcg ttatcgcaca cgatttgaca ccttcagata ctgctcaact taacaaacaa    360

tttgtaaaag catttgttac aaatatcggt ggtcgtacaa gtcactcagc tatcatggca    420

cgtacacttg agatcgctgc ggtacttgga acaaatgata ttacaaaacg tgttaaagat    480

ggtgatgtga ttgccgttaa tggtatcact ggtgaagtga ttatcgatcc aagcgaagat    540

caagtacttg cttttaaaga agctggtgcg gcttatgcca aacaaaaagc agagtggtct    600

ctccttaaag atgcgcatac tgaaacagct gatggcaaac actttgaatt ggctgctaat    660

atcggtacac ctaaagacgt tgaaggtgtt aatggcaatg gcgctgaagc tgttggcctt    720

taccgtactg agttcttgta catggattct caagacttcc caactgaaga cgaacaatac    780

gaagcttaca aggcagtgct tgaaggcatg aatggcaaac ctgttgtggt tcgtacgatg    840

gatattggtg gcgacaagga acttccttac tttgaccttc caaaagaaat gaatccattc    900

cttggtttcc gtgctcttcg tatttccatc tctgaaactg gggatgccat gttccgcaca    960

caaatgcgtg cgcttcttcg tgcctctgtt cacggacaac ttcgtattat gttcccaatg   1020

gttgcccttc ttaaagaatt ccgtgctgca aaagcagtct ttgatgaaga aaaagcaaac   1080

ttgcttgcag aaggcgttgc ggttgctgat gacatccaag ttggtatcat gattgagatt   1140

cctgcagctg ctatgcttgc agaccaattt gctaaggaag ttgatttctt ctcaattgga   1200

acaaacgacc ttatccaata cactatggca gcagaccgta tgaacgaaca agtatcatac   1260

ctttaccaac catacaaccc atcaatatta cgtttgatca acaatgtgat caaagcagcg   1320

cacgctgaag gtaaatgggc aggtatgtgt ggtgagatgg caggtgacca acaagctgt    1379
```

<210> SEQ ID NO 14
<211> LENGTH: 1378
<212> TYPE: DNA
<213> ORGANISM: Group A Streptococcus
<220> FEATURE:
<223> OTHER INFORMATION: ptsI sequence from isolate no. 1

<400> SEQUENCE: 14

-continued

```
gttatccgtg aaaatgcagt agaaagctta ggtgaagaag cagcagccgt ttttgatgcc     60
catttaatgg ttcttgctga tccagaaatg atcagccagg ttaaagaaac gattcgcgca    120
aaacaaacga atgcagaaac aggtcttaaa gaagtgactg acatgttcat caccatcttt    180
gaaggcatgg aagataaccc atacatgcaa gaacgtgcag cggacatccg cgacgttgca    240
aagcgtgtgt tggctcacct tttaggtgta aaacttccaa atccagctac aatcaatgaa    300
gaatcaatcg ttatcgcaca cgatttgaca ccttcagata ctgctcaact taacaaacaa    360
tttgtaaaag catttgttac aaatatcggt ggtcgtacaa gtcactcagc tatcatggca    420
cgtacacttg agatcgctgc ggtacttgga acaaatgata ttacaaaacg tgttaaagat    480
ggtgatgtga ttgccgttaa tggtatcact ggtgaagtga ttatcgatcc aagcgaagat    540
caagtacttg cttttaaaga agctggtgcg gcttatgcca aacaaaaagc agagtggtct    600
ctccttaaag atgcgcatac tgaaacagct gatggcaaac actttgaatt ggctgctaat    660
atcggtacgc ctaaagacgt tgaaggtgtt aatgacaatg gcgctgaagc tgttggcctt    720
taccgtactg agttcttgta catggattct caagacttcc caactgaaga cgaacaatac    780
gaagcttaca aggcagtgct tgaaggcatg aatggcaaac ctgttgtggt tcgtacgatg    840
gatattggtg gcgacaagga acttccttac tttgaccttc caaaagaaat gaatccattc    900
cttggtttcc gtgctcttcg tatttccatc tctgaaactg gggatgccat gttccgcaca    960
caaatgcgtg cgcttcttcg tgcctctgtt cacggacaac ttcgtattat gttcccaatg   1020
gttgcccttc ttaaagaatt ccgtgctgca aaagcaatct ttgatgaaga aaaagcaaac   1080
ttgcttgcag aaggcgttgc ggttgctgat gacatccaag ttggtatcat gattgagatt   1140
cctgcagctg ctatgcttgc agaccaattt gctaaggaag ttgatttctt ctcaattgga   1200
acaaacgacc ttatccaata cactatggca gcagatcgta tgaacgaaca agtatcatac   1260
ctttaccaac catacaaccc atcaatatta cgtttgatca acaatgtgat caaagcagcg   1320
cccgctgaag gtaaatgggc aggtatgtgt ggtgagatgg caggtgacca acaagctg     1378
```

<210> SEQ ID NO 15
<211> LENGTH: 1393
<212> TYPE: DNA
<213> ORGANISM: Group A Streptococcus
<220> FEATURE:
<223> OTHER INFORMATION: ptsI sequence from isolate no. 3

<400> SEQUENCE: 15

```
tgttatccgt gaaaatgcag tagaaagctt aggtgaagaa gcagcagccg tttttgatgc     60
ccatttaatg gttcttgctg atccagaaat gatcagccag gttaaagaaa cgattcgcgc    120
aaaacaaacg aatgcagaaa caggtcttaa agaagtgact gacatgttca tcaccatctt    180
tgaaggcatg gaagataacc catacatgca agaacgtgca gcggacatcc gcgacgttgc    240
aaagcgtgtg ttggctcacc ttttaggtgt aaaacttcca aatccagcta caatcaatga    300
agaatcaatc gttatcgcac acgatttgac accttcagat actgctcaac ttaacaaaca    360
atttgtaaaa gcatttgtta caaatatcgg tggtcgtaca agtcactcag ctatcatggc    420
acgtacactt gagatcgctg cggtacttgg aacaaatgat attacaaaac gtgttaaaga    480
tggtgatgtg attgccgtta atggtatcac tggtgaagtg attatcgatc caagcgaaga    540
tcaagtactt gcttttaaag aagctggtgc ggcttatgcc aaacaaaaag cagagtggtc    600
tctccttaaa gatgcgcata ctgaaacagc tgatggcaaa cactttgaat tggctgctaa    660
```

-continued

```
tatcggtacg cctaaagacg ttgaaggtgt taatgacaat ggcgctgaag ctgttggcct    720

ttaccgtact gagttcttgt acatggattc tcaagacttc ccaactgaag acgaacaata    780

cgaagcttac aaggcagtgc ttgaaggcat gaatggcaaa cctgttgtgg ttcgtacgat    840

ggatattggt ggcgacaagg aacttcctta ctttgacctt ccaaaagaaa tgaatccatt    900

ccttggtttc cgtgctcttc gtatttccat ctctgaaact ggggatgcca tgttccgcac    960

acaaatgcgt gcgcttcttc gtgcctctgt tcacggacaa cttcgtatta tgttcccaat   1020

ggttgccctt cttaaagaat tccgtgctgc aaaagcaatc tttgatgaag aaaaagcaaa   1080

cttgcttgca gaaggcgttg cggttgctga tgacatccaa gttggtatca tgattgagat   1140

tcctgcagct gctatgcttg cagaccaatt tgctaaggaa gttgatttct tctcaattgg   1200

aacaaacgac cttatccaat acactatggc agcagatcgt atgaacgaac aagtatcata   1260

cctttaccaa ccatacaacc catcaatatt acgtttgatc aacaatgtga tcaaagcagc   1320

gcacgctgaa ggtaaatggg caggtatgtg tggtgagatg gcaggtgacc aacaagctgt   1380

tccacttctt gtc                                                      1393
```

```
<210> SEQ ID NO 16
<211> LENGTH: 1379
<212> TYPE: DNA
<213> ORGANISM: Group A Streptococcus
<220> FEATURE:
<223> OTHER INFORMATION: ptsI sequence from isolate no. 1

<400> SEQUENCE: 16

tgttatccgt gaaaatgcag tagaaagctt aggtgaagaa gcagcagccg tttttgatgc     60

ccatttgatg gttcttgctg atccagaaat gatcagccag gttaaagaaa cgattcgcgc    120

aaaacaaacg aatgcagaaa caggtcttaa agaagtgact gacatgttca tcaccatctt    180

tgaaggcatg gaagataacc catacatgca agaacgtgca gcggacatcc gcgacgttgc    240

aaaacgtgtg ttggctcacc ttttaggtgt aaaacttcca aatccagcta caatcaatga    300

agaatcaatc gttatcgcac acgatttgac accttcagat actgctcaac ttaacaaaca    360

atttgtaaaa gcatttgtta caaatatcgg tggtcgtaca agtcactcag ctatcatggc    420

acgtacactt gagatcgctg cggtacttgg aacaaatgat attacaaaac gtgttaaaga    480

tggtgatgtg attgccgtta atggtatcac tggtgaagtg attatcgatc caagcgaaga    540

tcaagtactt gcttttaaag aagctggtgc ggcttatgcc aaacaaaaag cagagtggtc    600

tctccttaaa gatgcgcata ctgaaacagc tgatggcaaa cactttgaat tggctgctaa    660

tatcggtacg cctaaagacg ttgaaggtgt taatgacaat ggcgctgaag ctgttggcct    720

ttaccgtact gagttcttgt acatggattc tcaagacttc ccaactgaag acgaacaata    780

cgaagcttac aaggcagtgc ttgaaggcat gaatggcaaa cctgttgtgg ttcgtacaat    840

ggatattggt ggagataagg aacttcctta ctttgacctt ccaaaagaaa tgaacccatt    900

cctcggtttc cgtgctcttc gtatctcaat ctctgaaact ggggatgcca tgttccgcac    960

acaaatgcgt gcgcttcttc gcgcctctgt tcacggacaa cttcgtatca tgttcccaat   1020

ggtagcactt cttaaagaat tccgtgctgc aaaagcaatc tttgacgaag aaaaagcaaa   1080

cttgcttgca gaaggcgttg cggttgctga tgacatccaa gttggtatca tgattgagat   1140

tcctgcagct gctatgcttg cagaccaatt tgctaaggaa gttgatttct tctcaattgg   1200

aacaaacgac cttatccaat acactatggc agcagaccgt atgaacgaac aagtatcata   1260

cctttaccaa ccatacaacc catcaatatt acgtttgatc aacaatgtga tcaaagcagc   1320
```

-continued

```
gcacgctgaa ggtaaatggg caggtatgtg tggtgagatg gcaggtgacc aacaagctg    1379


<210> SEQ ID NO 17
<211> LENGTH: 1447
<212> TYPE: DNA
<213> ORGANISM: Group A Streptococcus
<220> FEATURE:
<223> OTHER INFORMATION: ptsI sequence from isolate no. 11

<400> SEQUENCE: 17

tgttatccgt gaaaatgcag tagaaagctt aggtgaagaa gcagcagccg tttttgatgc      60

ccatttgatg gttcttgctg atccagaaat gatcagccag gttaaagaaa cgattcgcgc     120

aaaacaaacg aatgcagaaa caggtcttaa agaagtgact gacatgttca tcaccatctt     180

tgaaggcatg gaagataacc catacatgca agaacgcgca gcggacatcc gcgacgttgc     240

aaaacgtgtg ttggctcacc ttttaggtgt aaaacttcca aatccagcta caatcaatga     300

agaatcaatc gttatcgcac acgatttgac accttcagat actgctcaac ttaacaaaca     360

atttgtaaaa gcatttgtta caaatatcgg tggtcgtaca agtcactcag ctatcatggc     420

acgtacactt gagatcgctg cggtacttgg aacaaatgat attacaaaac gtgttaaaga     480

tggtgatgtg attgccgtta atggtatcac tggtgaagtg attatcgatc caagcgagga     540

tcaagtactt gcttttaaag aagctggtgc ggcttatgcc aaacaaaaag cagagtggtc     600

tctccttaaa gatgcgcata ctgaaacagc tgatggcaaa cactttgaat tggctgctaa     660

tatcggtacg cctaaagatg ttgaaggtgt taatgacaat ggtgctgaag ctgttggcct     720

ttaccgtact gagttcttgt acatggattc tcaagacttc ccaactgaag acgaacaata     780

cgaagcttac aaggcagtgc ttgaaggcat gaatggcaaa cctgttgtgg ttcgtacaat     840

ggatattggt ggagataagg aacttcctta ctttgacctt ccaaaagaaa tgaacccatt     900

cctcggtttc cgtgctcttc gtatctcaat ctctgaaact ggggatgcca tgttccgcac     960

acaaatgcgt gcgcttcttc gtgcctctgt tcacggacaa cttcgtatca tgttcccaat    1020

ggtagcactt cttaaagaat tccgtgctgc aaaagcaatc tttgacgaag aaaaagcaaa    1080

cttgcttgca gaaggcgttg cggttgctga tgacatccaa gttggtatca tgattgagat    1140

tcctgcagct gctatgcttg cagaccaatt tgctaaggaa gttgatttct tctcaattgg    1200

aacaaacgac cttatccaat acactatggc agcagaccaa tttgctaagg aagttgattt    1260

cttctcaatt ggaacaaacg accttatcca atacactatg gcagcagacc gtatgaacga    1320

acaagtatca tacctttacc aaccatacaa cccatcaata ttacgtttga tcaacaatgt    1380

gatcaaagca gcgcacgctg aaggtaaatg ggcaggtatg tgtggtgaga tggcaggtga    1440

ccaacaa                                                              1447
```